US011721440B1

(12) United States Patent
Shan et al.

(10) Patent No.: US 11,721,440 B1
(45) Date of Patent: Aug. 8, 2023

(54) VIRTUAL SIDEKICK IN A HEALTH MANAGEMENT PLATFORM USER INTERFACE

(71) Applicant: Verily Life Sciences LLC, Mountain View, CA (US)

(72) Inventors: Peilun Shan, San Francisco, CA (US); Aurora Adkins, Redwood City, CA (US); Thomas Rudick, San Francisco, CA (US); Lucy Boyd Schachter, Jamaica Plain, MA (US); Bella Powers, Redwood City, CA (US); Nikhil Roy, Sunnyvale, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 24 days.

(21) Appl. No.: 17/208,685

(22) Filed: Mar. 22, 2021

Related U.S. Application Data

(60) Provisional application No. 62/994,031, filed on Mar. 24, 2020.

(51) Int. Cl.
| | |
|---|---|
| *G06F 3/048* | (2013.01) |
| *G16H 50/30* | (2018.01) |
| *G06F 3/14* | (2006.01) |
| *G06F 9/451* | (2018.01) |

(52) U.S. Cl.
CPC .............. *G16H 50/30* (2018.01); *G06F 3/14* (2013.01); *G06F 9/451* (2018.02)

(58) Field of Classification Search
CPC ............ G16H 50/30; G06F 9/451; G06F 3/14
See application file for complete search history.

(56) References Cited

U.S. PATENT DOCUMENTS

| | | | |
|---|---|---|---|
| 9,053,483 B2* | 6/2015 | Geisner | G02B 27/017 |
| 11,216,857 B2* | 1/2022 | Lokesh | G06Q 30/0613 |
| 2007/0067104 A1* | 3/2007 | Mays | G01C 21/3647 |
| | | | 701/437 |
| 2014/0125678 A1* | 5/2014 | Wang | A63F 13/80 |
| | | | 345/473 |
| 2016/0314279 A1* | 10/2016 | Slepian | G06T 11/206 |
| 2017/0147775 A1* | 5/2017 | Ohnemus | G16H 20/30 |
| 2017/0368413 A1* | 12/2017 | Shavit | A61B 5/1123 |
| 2018/0068577 A1* | 3/2018 | Javanbakht | H04N 7/152 |

* cited by examiner

*Primary Examiner* — Mahelet Shiberou
(74) *Attorney, Agent, or Firm* — Perkins Coie LLP

(57) ABSTRACT

A user interface for a health management platform is described that includes a virtual sidekick configured to assist a patient in managing a chronic health condition. The virtual sidekick may represent an individual (not necessarily the patient) that is facing similar challenges as the patient such as the same chronic health condition as the patient. In some embodiments, the virtual sidekick can be presented in a virtual scene that includes one or more reverse augmented realty elements that are indicative of a physical context of the patient. For example, the virtual scene may depict visual elements indicative of the patient's physical location and/or weather conditions at the patient's physical location. Data used to personalize and dynamically animate the virtual sidekick to assist the patient in managing a chronic health condition can come from multiple different sources.

25 Claims, 13 Drawing Sheets

VIRTUAL SIDEKICK IN A HEALTH MANAGEMENT PLATFORM USER INTERFACE

CROSS REFERENCE TO RELATED APPLICATION

This application claims benefit to U.S. Provisional Application No. 62/994,031, filed Mar. 24, 2020 and titled "VIRTUAL SIDEKICK IN A HEALTH MANAGEMENT PLATFORM USER INTERFACE," which is incorporated by reference herein in its entirety.

TECHNICAL FIELD

The disclosed teachings relate to techniques for self-management of chronic health conditions. The disclosed teachings more particularly relate to a graphical user interface associated with a health management platform for assisting a user in self-management of a chronic health condition.

BACKGROUND

Quality of life for patients facing chronic health conditions such as diabetes can be significantly improved through taking active measures to manage such conditions. Active measures for managing a chronic health condition can include, for example, exercise, maintaining a healthy diet, actively monitoring physiological data, taking medications as prescribed, and other measures. Clinical physicians and health coaches can help patients manage chronic health conditions; however, due to infrequent interaction, patients are left to take most active measures on their own.

DETAILED DESCRIPTION

Overview

Figure 1:
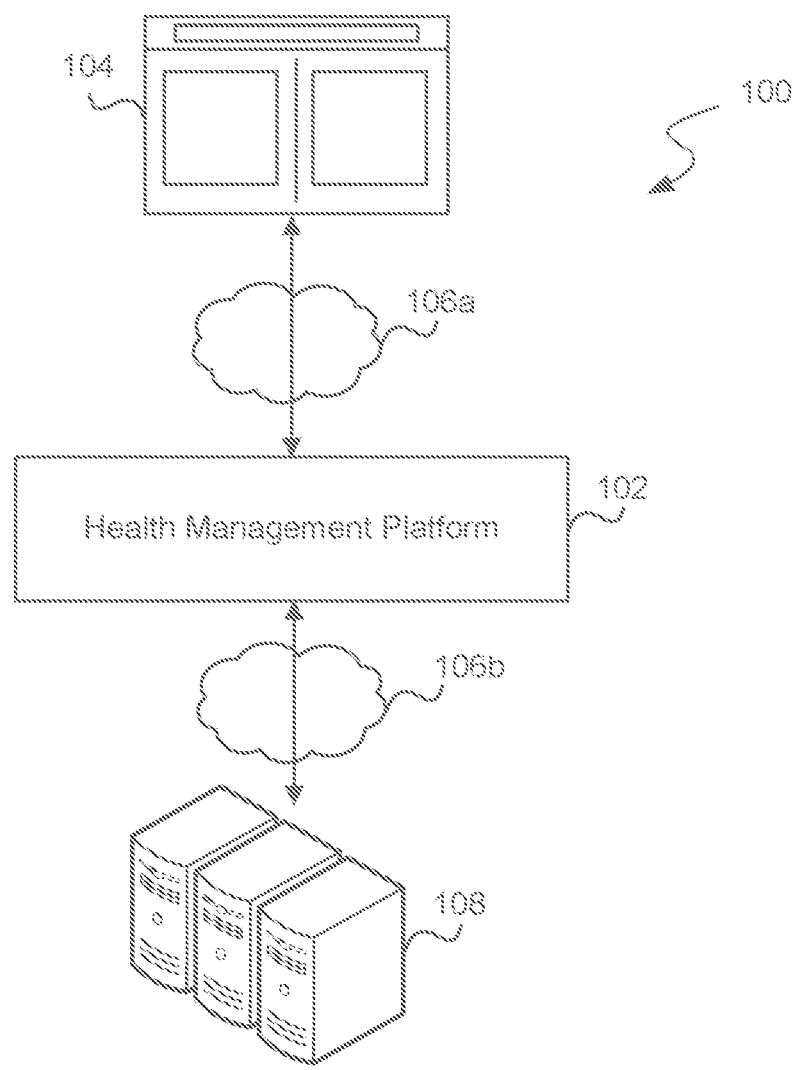
FIG. 1 shows an example network environment that includes a health management platform.

A patient with a chronic health condition such as diabetes may need encouragement and motivation to help manage his or her chronic health condition. Clinical interactions with patients are infrequent, so it can be difficult for a clinician to follow transitions in the health state of a patient and intervene to assist the patient in managing a chronic health condition. Automated solutions involving virtual health coaches and or virtual doctors have been developed; however, existing automated solutions can be cold and clinical and can turn the patient away, thereby affecting the management of that patient's chronic health condition.

Introduced here, therefore, is a computer-implemented health management platform that includes a virtual sidekick configured to assist a patient in managing a chronic health condition. As used herein, a "virtual sidekick" refers to a computer-simulated character or other entity that can be presented to a patient via an interface of the health management platform. For example, actions and/or appearances of a virtual sidekick can be simulated using one or more computer programs and visual representations based on such simulations of the virtual sidekick can be rendered and displayed to a patient via a display of a user computing device.

The virtual sidekick can "assist" a patient in managing a chronic health condition in various direct and/or indirect ways. Direct assistance in managing a chronic health condition may include, for example, explicit recommendations presented by the virtual sidekick for the patient to perform certain activities (e.g., exercise), eat certain foods (e.g., healthier options), take health measurements (e.g., take blood glucose measurements), consult with health professionals, review educational materials, etc. For example, if the patient needs to exercise more, the virtual sidekick can explicitly recommend, through visual and/or audible communication, a particular exercise for the user to perform Conversely, indirect assistance may refer to various indirect actions, visual cues, passive interactions, etc. that are tailored to subtly influence a patient's behavior in a certain direction to manage a chronic health condition. For example, in some embodiments, the appearance and/or actions by the virtual sidekick can be tailored to build a relationship between the virtual sidekick and the patient thereby increasing the behavioral influence the virtual sidekick has on the patient. In some embodiments, the virtual sidekick may be presented as an individual (not necessarily the patient) that is facing similar challenges as the patient. For example, if the patient has diabetes, the virtual sidekick can be depicted as also having diabetes. In this sense, and in contrast to a virtual health coach or virtual doctor, the virtual sidekick can act as a partner to the patient in the patient's journey to manage his or her chronic health condition. In some embodiments, the virtual sidekick may be configured to be fallible to enable a patient to relate to the virtual sidekick. For example, the virtual sidekick may falter or make mistakes to provide a contrast to the patient without normalizing failures. In some embodiments, the virtual sidekick can be presented in a virtual scene that includes one or more reverse augmented realty elements that are indicative of a physical context of the patient. This can help instill, in the patient, a feeling of proximity to the virtual sidekick. For example, the virtual scene may depict visual elements indicative of the patient's physical location and/or weather conditions at the patient's physical location. In some embodiments, the virtual sidekick may dynamically respond to the patient, for example, through audible and/or visual expressions or other actions.

Data used to personalize and dynamically animate the virtual sidekick to assist the patient can come from multiple different sources including a computing device associated with the patient, various sensors, health monitoring devices, fitness tracking devices, social media services, location services, weather services, internet of things (IOT) devices, and various other sources.

Terminology

References in this description to "an embodiment" or "one embodiment" mean that the particular feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the words "comprise" and "comprising" are to be construed in an inclusive sense rather than an exclusive or exhaustive sense (i.e., in the sense of "including but not limited to"). The terms "connected," "coupled," or any variant thereof is intended to include any connection or coupling between two or more elements, either direct or indirect. The coupling/connection can be physical, logical, or a combination thereof. For example, devices may be electrically or communicatively coupled to one another despite not sharing a physical connection.

The term "based on" is also to be construed in an inclusive sense rather than an exclusive or exhaustive sense. Thus, unless otherwise noted, the term "based on" is intended to mean "based at least in part on."

The term "module" refers broadly to software components, hardware components, and/or firmware components. Modules are typically functional components that can generate useful data or other output(s) based on specified input(s). A module may be self-contained. A computer program may include one or more modules. Thus, a computer program may include multiple modules responsible for completing different tasks or a single module responsible for completing all tasks.

When used in reference to a list of multiple items, the word "or" is intended to cover all of the following interpretations: any of the items in the list, all of the items in the list, and any combination of items in the list.

The sequences of operations performed in any of the processes described here are exemplary. However, unless contrary to physical possibility, the operations may be performed in various sequences and combinations. For example, operations could be added to, or removed from, the processes described here. Similarly, operations could be replaced or reordered. Thus, descriptions of any processes are intended to be open-ended.

Technology Overview

FIG. 1 illustrates an example network environment 100 that includes a health management platform 102. A user can interface with the health management platform 102 via an interface 104 to access the various functionalities described herein. For example, in some embodiments, the health management platform 102 is associated with one or more computer programs configured to present a virtual sidekick to a user via a graphical user interface (GUI). A "user" may refer to a patient with a chronic health condition and/or another person with an interest in the patient's management of the chronic health condition such as a physician, health coach, etc. The health management platform 102 may be connected to one or more networks 106a-b. The network(s) 106a-b can include local area networks (LANs), wireless LANs (WLANs), wide area networks (WANs), metropolitan area networks (MANs), cellular networks, the Internet, etc. The health management platform 102 may also communicate with other computing devices over a short-range communication protocol, such as Bluetooth™ or Near Field Communication (NFC).

An individual can access various functionalities provided by the health management platform via interface 104. The interface 104 may be accessible via one or more of a web browser, a desktop software program, a mobile application, an over-the-top (OTT) application, or any other type of application configured to present an interface to a user. Accordingly, the interface 104 may be accessed by the user on a user computing device such as a personal computer, tablet computer, personal digital assistant (PDAs), mobile phone, game console (e.g., Sony PlayStation™ or Microsoft Xbox™), music player (e.g., Apple iPod Touch™), wearable electronic device (e.g., a watch or fitness band), network-connected ("smart") device (e.g., a television or home assistant device), virtual/augmented reality system (e.g., a head-mounted display such as Oculus Rift™ and Microsoft Hololens™), or some other electronic device.

In some embodiments, the health management platform 102 is hosted locally. That is, one or more of the computer programs associated with the health management platform 102 may reside on the computing device used to access the interface 104. For example, the health management platform 102 may be embodied as a mobile application executing on a user's mobile phone. In some embodiments, one or more components of the health management platform 102 may be executed by a cloud computing service, for example, operated by Amazon Web Services™ (AWS), Google Cloud Platform™ Microsoft Azure™, or a similar technology. In such embodiments, the health management platform 102 may reside on a host computer server that is communicatively coupled to one or more content computer servers 108. The content computer server(s) 108 can include different types of data, user information (e.g., profiles, credentials, and health-related information), and other assets. Additionally, or alternatively, such information could be stored on the host computer server. In some embodiments, one portion of the health management platform 102 may be hosted locally while another portion is hosted remotely (e.g., at a cloud computing service). For example, the health management platform 102 may comprise a mobile application executing locally at mobile device as well as other applications executing at remote host/content servers. In such embodiments, the local and remote portions of the health management platform 102 may communicate with each other via one or more networks 106a-b.

Certain embodiments are described in the context of network-accessible interfaces. However, those skilled in the art will recognize that the interfaces need not necessarily be accessible via a network. For example, a computing device may be configured to execute a self-contained software program that does not require network access. Instead, the self-contained software program may cause necessary assets (e.g., physiological data, healthcare regimen data, processing operations, etc.) to be downloaded at a single point in time or on a periodic basis (e.g., weekly, hourly, or daily).

Figure 2:
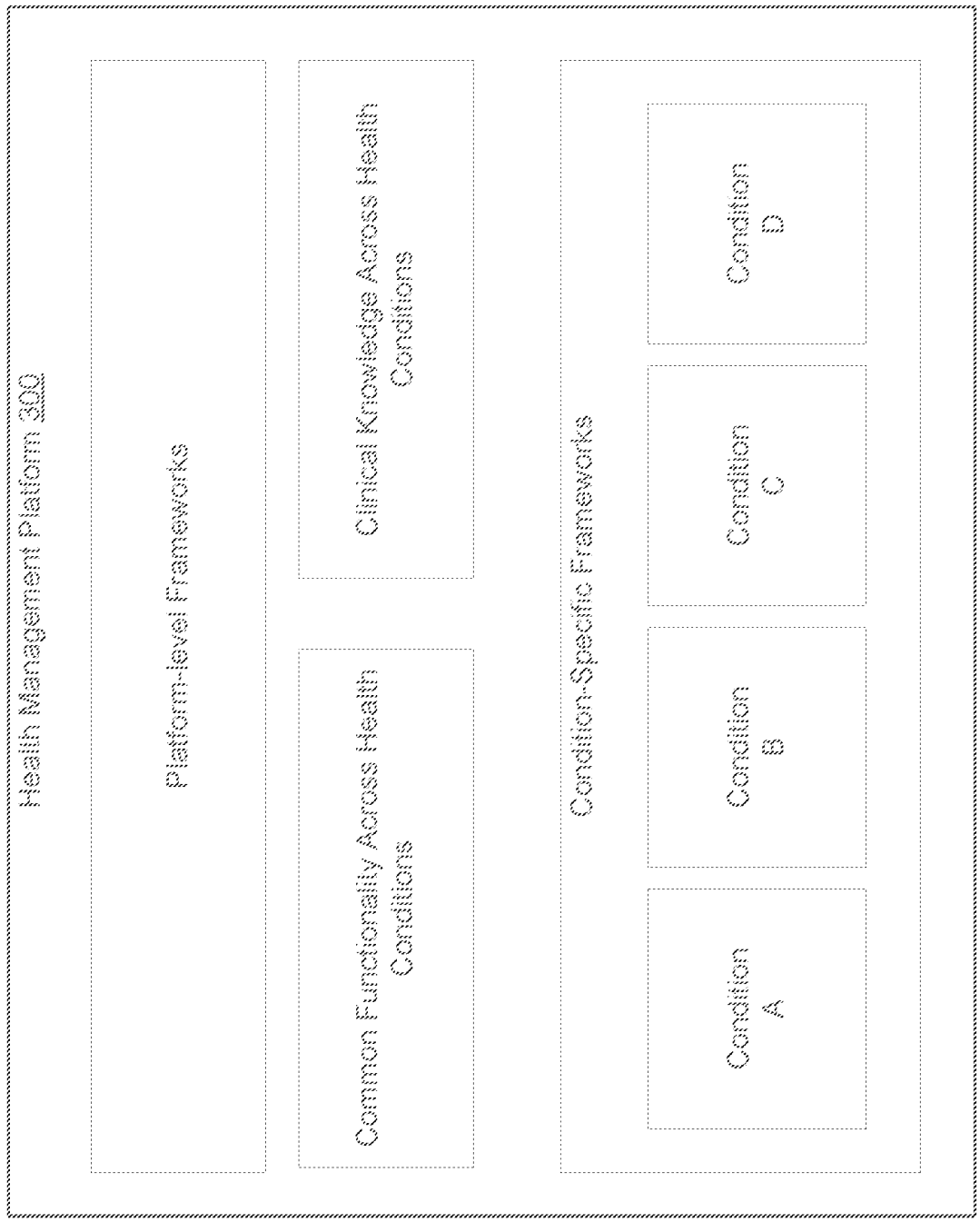
FIG. 2 shows a high-level architecture of an example health management platform.

In some embodiments, a health management platform 102 may be configured to assist users in managing multiple different chronic diseases (also referred to as health conditions). Examples of chronic diseases that may be managed using the health management platform 102 include diabetes, asthma, arthritis, cardiovascular disease, various cancers, etc. FIG. 2 shows a high-level architecture of an example health management platform 200 (e.g., similar to health management platform 102) that depicts an example organization of condition-specific frameworks. As shows in FIG. 2, the health management platform 200 may include multiple different condition-specific frameworks for managing specific chronic health conditions. Each condition-specific framework can be conceptualized as an application that can be run within the broader operating system of the health management platform 200. For example, a user with diabetes may utilize a diabetes-specific application within the health management platform 200 while another user with arthritis may utilize an arthritis-specific application. Each condition-specific framework may include specialized functionality (e.g., condition specific GUI features) and rely on specialized clinical knowledge associated with the condition. However, each condition-specific framework may also rely on higher level functionalities and/or clinical knowledge associated with the health management platform 200 that are common across the various different health conditions.

Figure 3:
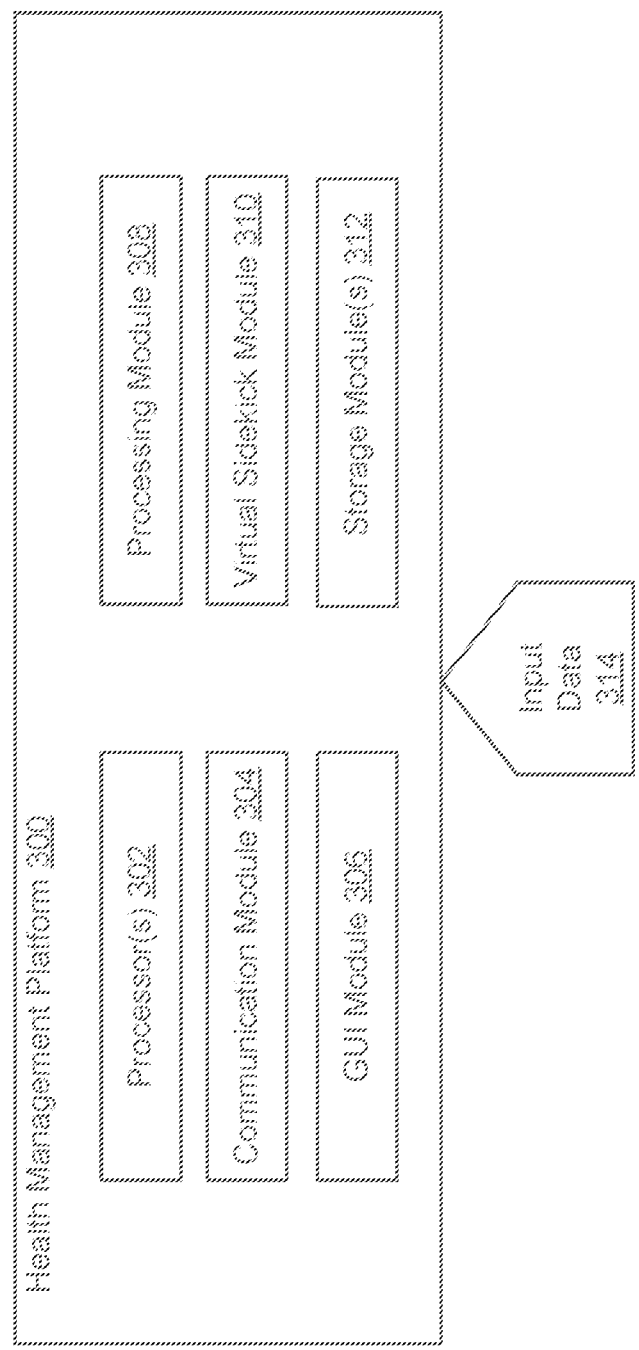
FIG. 3 shows another high-level architecture of an example health management platform.

FIG. 3 shows another high-level architecture of an example health management platform 300 (e.g., similar to health management platform 102). A user can interface with the health management platform 300 via an interface (e.g., similar to interface 104).

The health management platform 300 can include one or more processors 302, a communication module 304, a GUI module 306, a processing module 308, a virtual sidekick module 310, and one or more storage modules 312. In some embodiments, a single storage module includes multiple computer programs for performing different operations (e.g., format conversion, temporal alignment, statistical analysis), while in other embodiments each computer program is hosted within a separate storage module. Embodiments of the diabetes management platform 300 may include some or all of these components, as well as other components not shown here.

The processor(s) 302 can execute modules (e.g., the processing module 308 and the virtual sidekick module 310) from instructions stored in the storage module(s) 312, which can be any device or mechanism capable of storing information. The communication module 304 can manage communications between various components of the health management platform 300. The communication module 304 can also manage communications between the computing device on which the health management platform 300 resides and another computing device.

For example, the health management platform 300 may reside on a mobile phone in the form of a mobile application. In such embodiments, the communication module 304 can facilitate communication with a network-accessible computer server responsible for supporting the mobile application. The communication module 304 may facilitate communication with various data sources by using application programming interfaces (APIs), bulk data interfaces, etc.

As another example, the health management platform 300 may reside on a server system that includes one or more network-accessible computer servers. In such embodiments, the communication module 304 can communicate with a software program executing on the computing device associated with the individual. Those skilled in the art will recognize that the components of the health management platform 300 can be distributed between the server system and the computing device associated with the individual in various manners. For example, some data may reside on the computing device of the individual, while other data may reside on the server system.

The GUI module 306 can generate the interface(s) through which an individual can interact with the health management platform 300. For example, an interface may include a visual representation of a virtual sidekick that is simulated by the virtual sidekick module 310. As another example, an interface may include a visual representation of a virtual scene that includes the visual representation of the virtual sidekick along with one or more reverse augmented reality elements.

The processing module 308 can apply one or more operations to input data 314 acquired by the health management platform 300 to provide certain functionalities described herein.

The virtual sidekick module 310 may comprise one or more computer programs operable to simulate a virtual sidekick. In some embodiments, such computer programs may include instructions for performing one or more predefined interaction scripts in response to detected events or conditions. For example, instructions associated with a computer program may cause a visual representation of the virtual sidekick to depict the virtual sidekick performing a predefined action (e.g., walking) in response to detecting, based on input data, a condition or event (e.g., the user walking). Alternatively, or in addition, the computer program used to simulate the virtual sidekick may include or utilize one or more artificial intelligence models. In such embodiments, input data (and/or contextual information) may be fed into an artificial intelligence model that generates outputs that cause the presentation of the virtual sidekick in the GUI to dynamically update.

Figure 4:
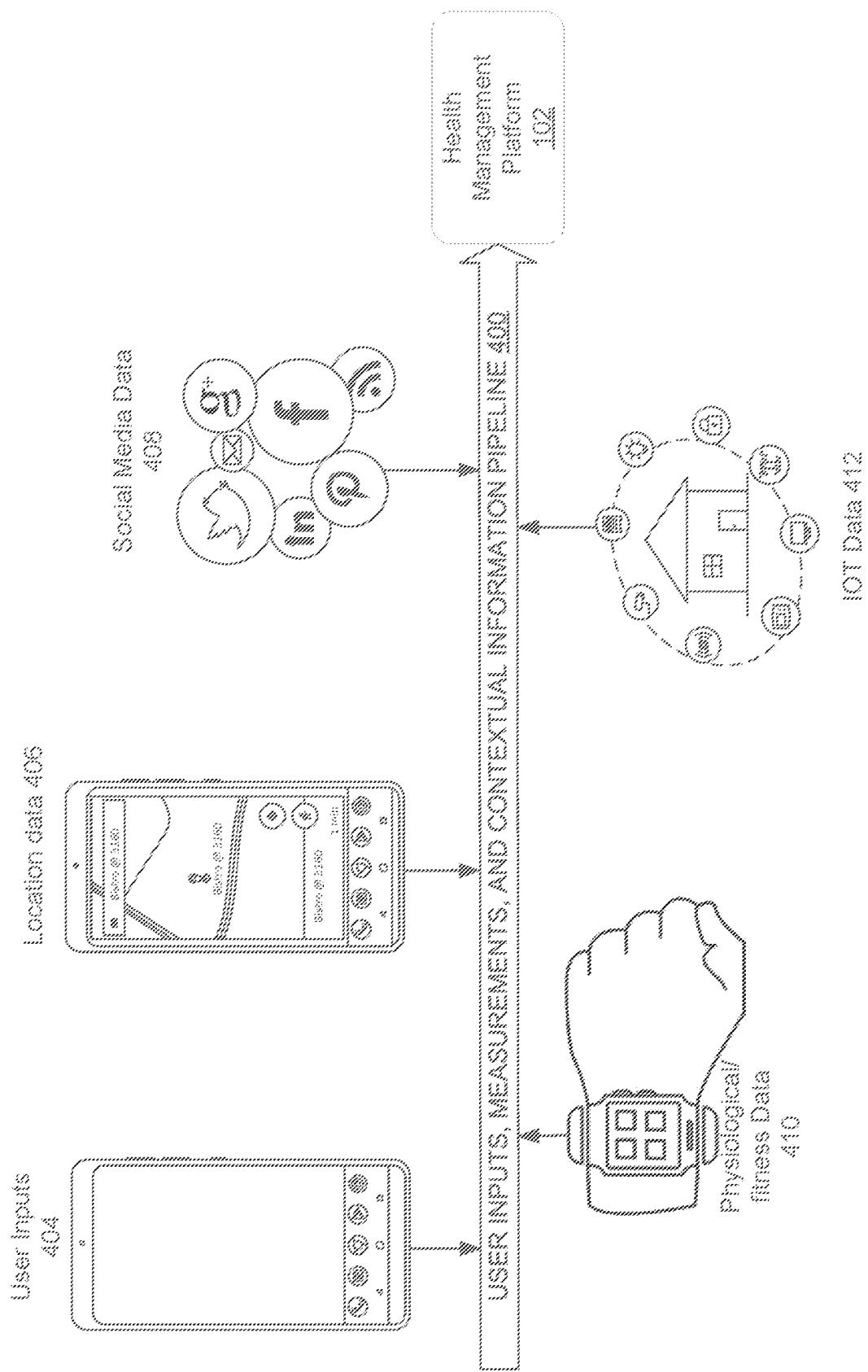
FIG. 4 shows a block diagram illustrating an example data pipeline that may be utilized by a health management platform.

The input data 314 may comprise data from multiple different sources. FIG. 4 shows a block diagram illustrating an example data pipeline 400 comprising user inputs and other contextual data that may be utilized by a health management platform to provide certain functionalities described herein. The data pipeline 400 sources user inputs and/or contextual information from various diverse sources such as a user computing device, health monitoring devices (e.g., fitness trackers, glucometers), other network connected devices (e.g., IOT devices), online services (e.g., location services, social media, etc.), or any other suitable data sources. The data pipeline 400 may feed a health management platform 102 using one or more communication channels (e.g., computer networks 106a-b).

User input data 404 may include any data input by the user via the user interface 104 associated with the health management platform 102. For example, the health management platform 102 may present a GUI to the user via interface 104 which the user can interact with. The user interactions with interface 104 may be registered as user inputs 404.

Location data 406 may include a data indicative of a user's physical location and may be determined, for example, using a GPS receiver in a computing device associated with the user. The location information 406 can be used to determine, for example, where the user is located to determine what the weather is like at the user's location.

In response to determining a user location, an online weather service can be accessed to determine weather data at the user's location. The location data may also be used to determine, for example, whether the user visited a location that is relevant to the user's chronic health condition such as doctor's office, a restaurant, or a gym. Such location data 406 may be used to, for example, present contextual information alongside a virtual assistant in a GUI.

Social media data 408 may include posts by or related to a patient and made available on social media. For example, a user may take a picture of his or her dinner and post it on Facebook™. The image or related content may be sent over the pipeline 400 to the health management platform 102. The image can be analyzed by the health management platform 102 to determine, for example, if a meal-based goal has been reached or to trigger, present contextual information regarding the user's meal via a GUI, trigger intervention challenges such as meal swap, etc.

Physiological/fitness data 410 may include data regarding a user's health and/or activity. Examples of physiological data include heart rate, blood glucose level, etc. Examples of other fitness-related (but not necessarily physiological) data include a type of exercise performed (e.g., running or jumping), a duration of the exercise (e.g., elapsed time), or other metrics associated with the exercise (e.g., distance traveled).

In some embodiments physiological data may be acquired from a health monitoring device. For example, a physiological data specifying the blood glucose level of an individual could be generated by a glucose monitoring device. Examples of glucose monitoring devices include continuous glucose monitors (e.g., Medtronic Enlite™ Sensor) and blood glucose meters (e.g., Bayer Contour™).

Similarly, other fitness related data may be acquired from a fitness tracking device. Examples of fitness tracking devices include mobile phones or smartwatches with motion tracking functionality or specialized fitness trackers such those offered by Fitbit™ A fitness tracking device may track a motion of a user using onboard motions sensors (e.g., one or more accelerometers) and analyze the motion to determine an activity state of the user (e.g., running vs. walking, vs stationary) and one or more fitness related metrics (e.g., distance traveled, duration of run, calories burned, etc.). In some embodiments, a fitness tracking device may include sensors such as a heart rate monitor configured to generate physiological data such as a heart rate.

In some embodiments, the data pipeline 400 may include IOT data 412 from one or more IOT devices such as smart appliances in the home. For example, IOT data 412 may include data from a smart refrigerator that indicates when a user opens the refrigerator door or a frequency that the user opens the refrigerator door. In other example, data from a smart assistant device (e.g., an Amazon Echo™) can be used to register voice commands from a user or determine a health state of the user through verbal inputs (e.g., "I feel well" or "I feel sick"). IOT data 412 may include contextual data from any other network-connected devices including environmental sensors, security cameras, energy monitoring devices, etc. that can be used to determine information about a state of the user.

In some embodiments, one or more of the data sources associated with the data pipeline 400 may continually upload data to the health management platform 102 so long as the data source remains communicatively to a computer system on which the health management platform 102 resides (e.g., via network connection). In other embodiments, one or more of the data sources may periodically upload input data to the health management platform 102 on a periodic basis (e.g., hourly, daily, weekly). In such embodiments, the input data may include multiple data sets for various time intervals (e.g., a first data set for a first time interval, a second data set for a second time interval, etc.). in some embodiments, a computer system associated with the health management platform may actively pull input data from one or more of the data sources (i.e., without requiring that the data sources upload data). In such embodiments, input data may be pulled continually as the data source remains communicatively to a computer system on which the health management platform 102 resides or may be pulled on a periodic basis (e.g., hourly, daily, weekly).

The diagram depicted in FIG. 4 is shown to illustrate the disparate types of input data that can be used by a health management platform; however, not all embodiments will utilize all the data sources shown in FIG. 4. To address privacy concerns associated with the handling of such data, the health management platform 102 is configured to conform with all applicable data privacy and health information laws and regulations. Further, to provide additional safeguards, the health management platform 102 can provide users with options to enable various privacy settings to, for example, specify which input data can be gathered, how such input data can be stored and processed, how the results of the processing of input data (e.g., contextual data) can be stored and used, etc. The privacy settings may also provide users with options to delete data (e.g., certain input data and/or contextual data). Such privacy settings may be adjusted by the user via a GUI associated with the health management platform 102 such as interface 104.

Virtual Sidekick in a Graphical User Interface of a Health Management Platform

Figure 5:
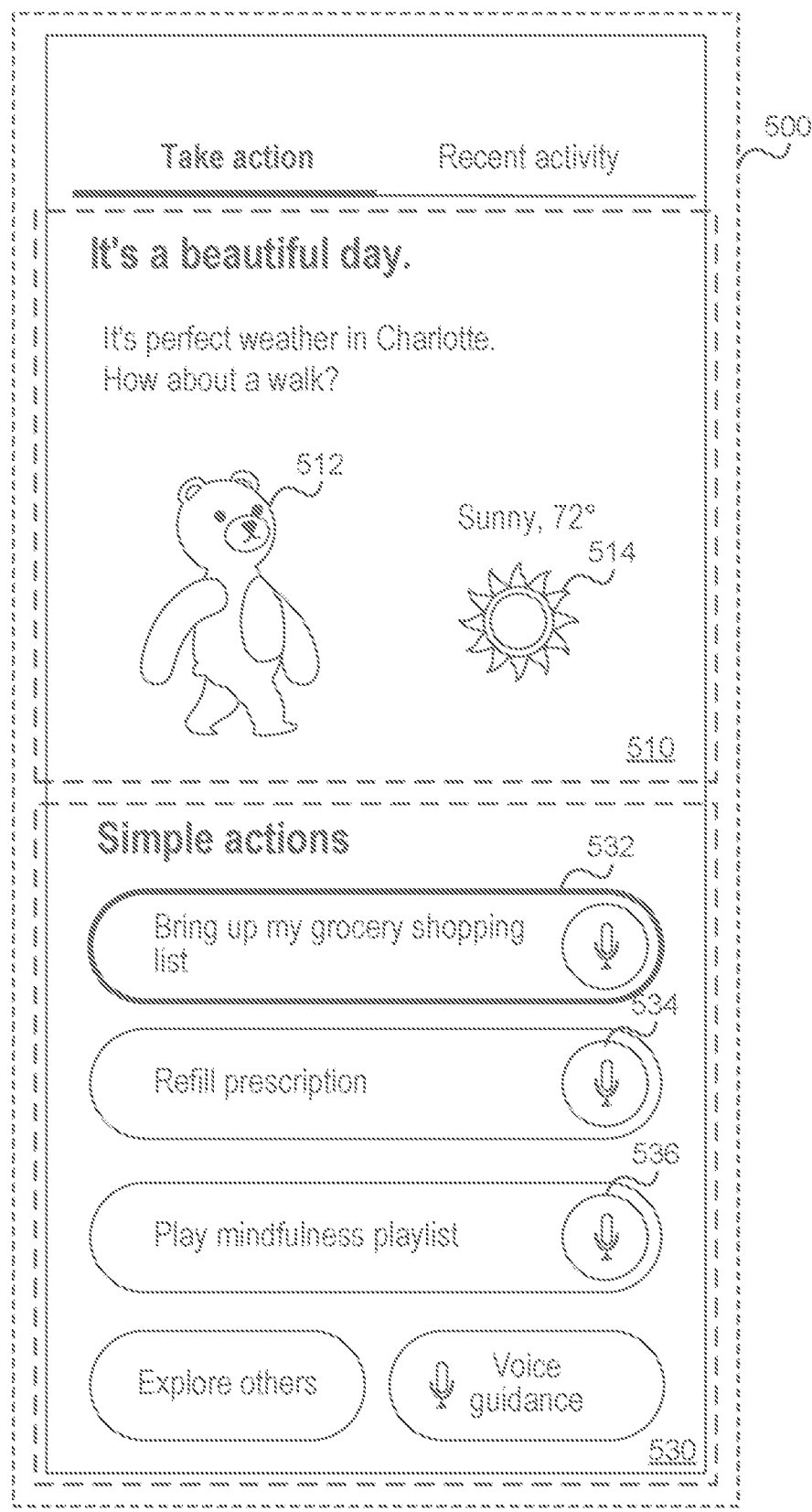
FIG. 5 shows a screen of an example graphical user interface of a health management platform that depicts a virtual sidekick.

FIG. 5 depicts an example GUI 500 that includes a virtual sidekick. The example GUI 500 may be part of an interface 104 associated with a health management platform 102. As shown in FIG. 5, a visual representation of the virtual sidekick 512 may be displayed in the GUI 500 as an animated character such as a stylized bear, although other embodiments may use different types of characters.

The virtual sidekick 512 may be presented as a partner or peer to a user of the health management platform 102 to assist the user in managing a chronic health condition such as diabetes. In some embodiments, to enhance the partner or peer relationship between the virtual sidekick 512 and the user, the virtual sidekick 512 may be depicted as facing the same challenges as the user. For example, if the user has a chronic health condition, the virtual sidekick 512 may be depicted, through actions and/or appearance, as having the same, or a substantially similar, chronic health condition. In this context, a substantially similar chronic health condition may refer to a disease that falls under a same disease category as a disease of a user. For example, if a user has type 1 diabetes, a substantially similar chronic health condition may include type 2 diabetes because both conditions fall under a broader disease category of "diabetes" which refers an impairment in the ability of the body to make and/or use insulin to regulate blood glucose levels. As another example, if the user has a first type of cancer, a substantially similar chronic health condition may include a second type of cancer that is different than the first type of cancer because both conditions fall under a broader disease category of "cancer" which refers to uncontrolled or abnormal cell division in the body.

In contrast with a virtual assistant, virtual health coach, or virtual physician, the virtual sidekick 512 is not intended to serve as an authority or expert to the user. The virtual sidekick 512 is instead intended to share the experience with the user of managing the user's chronic health condition. For example, the mood or health condition of the virtual sidekick 512 may be adjusted to correspond to a detected mood or health condition of the user. As another example, the virtual sidekick 512 may be depicted as performing certain activities associated with the management of a chronic health condition such as exercising, making dietary changes, taking health monitoring measurements, etc. Further, the virtual sidekick may be presented as fallible to enable the user to relate to the virtual sidekick 512. For example, the virtual sidekick 512 may be depicted as making a mistake while taking a blood glucose reading using a glucose monitoring device. In this sense, successes and failures by the user may correspond to successes and failures by the virtual sidekick 512, and vice versa. Such functionality may promote successful management by the user of his or her own health condition by encouraging the user to take responsibility for the well-being of the virtual sidekick 512.

In some embodiments, the visual representation of the virtual sidekick 512 may be depicted in the GUI 500 in a virtual scene that includes one or more visual representations of reverse augmented reality elements 514. In this context, a reverse augmented reality element may refer to one or more graphical elements that are indicative of a physical context of the user such as a physical location of the user, a weather condition at the physical location of the user, an object in proximity to the user, or an activity performed by the user. For example, FIG. 5 shows a visual representation of a reverse augmented reality element 514 in the form of a stylized sun that is representative of the sunny weather at the user's physical location in Charlotte. Other types of reverse augmented reality elements are described in more detail later.

In some embodiments, the visual representation of the virtual sidekick 512 and the visual representation of the one or more reverse augmented reality elements 514 are displayed in a first portion 510 of the GUI 500 while other interactive elements are displayed in other portions of the GUI 500. For example, as shown in FIG. 5, another portion 530 may include one or more interactive elements 532, 534, 536 through which the user may perform quick actions such as viewing a grocery list, refilling a prescription, or paying a music playlist. Such interactive elements 532, 534, 536 may be associated with other functionalities of health management platform 102 that are outside of the scope of the present disclosure.

In some embodiments, the portion 510 of the GUI 500 including the virtual sidekick 512 may be displayed first to the user before other portions of the GUI 500, for example, as depicted in FIG. 5. In an example embodiment, the portion 510 of the GUI 500 including the visual representation of the virtual sidekick 512 is displayed to the user as an initial page when an application associated with the health management platform 102 is started. In this way, the virtual sidekick 512 may be the first element that the user views when the user accesses the health management platform 102 via interface 104.

Figure 6:
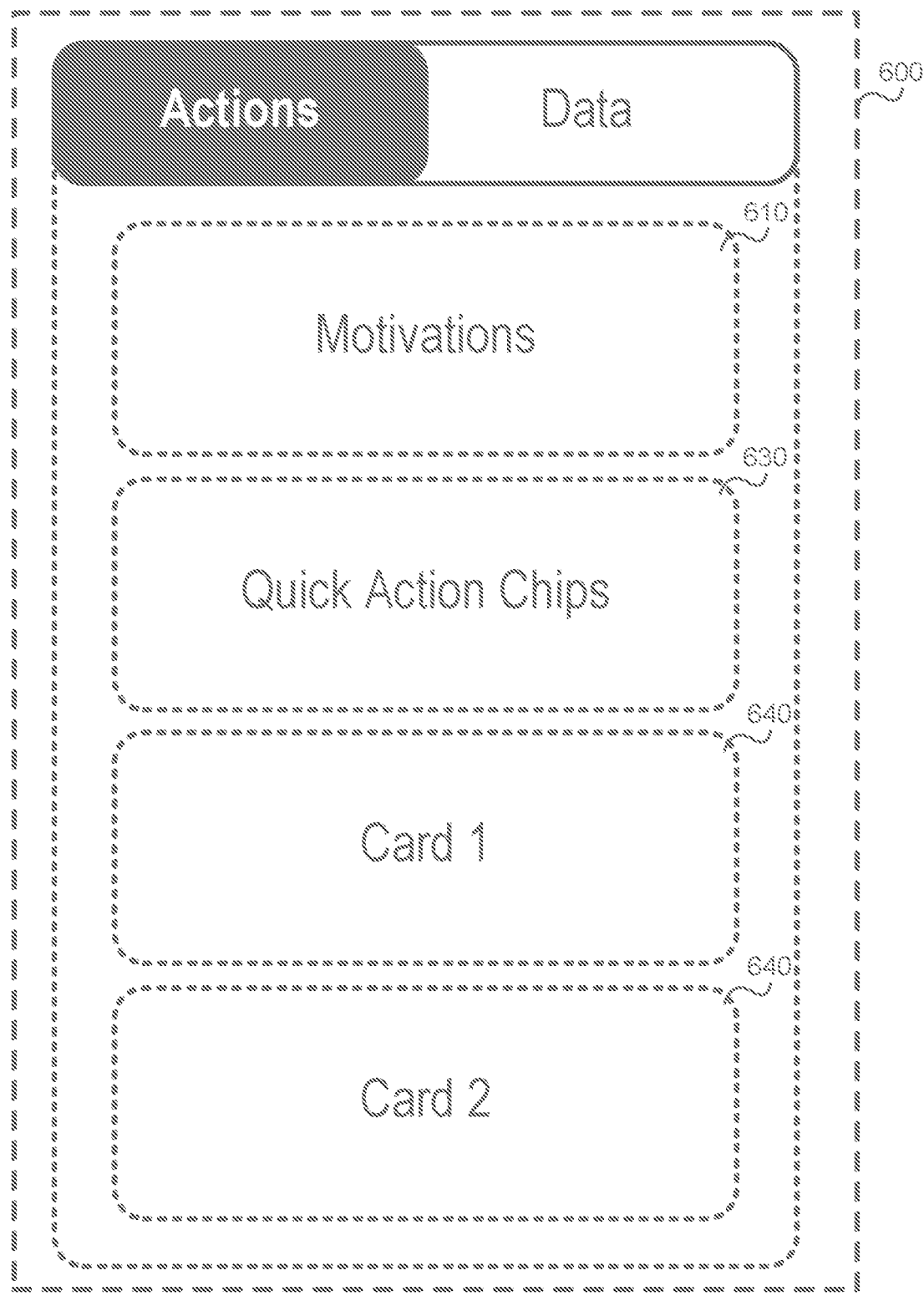
FIG. 6 shows an example template that may be utilized to configure a graphical user interface of a health management platform.

In some embodiments, the GUI 500 may be arranged according to one or more configurable templates. For example, FIG. 6 shows an example GUI template 600 that may be utilized to configure a GUI (e.g., GUI 500) associated with the health management platform 102. As shown in FIG. 6, the GUI template 600 includes several different portions such as a motivations portion 610, a quick actions portion 630, and one or more additional portions 640. The motivations portion 610 is arranged at the top of the GUI template 600 and may be used to display motivational functionalities of the health management platform 102 such as the visual representation of the virtual sidekick 512. Quick actions portion 630 is arranged below the motivations portion 610 and may be used to display one or more interactive graphical elements associated with quick actions that the user can perform via the health management platform 102 such as the interactive elements 532, 534, and 536. In some embodiments, the various portions 610, 630, and 640 of the example GUI template 600 may be rearranged to reconfigure how a GUI (e.g., GUI 500) is displayed to a user. In some embodiments, the GUI template 600 may be rearranged based on inputs by the user and/or automatically, for example, based on tracked activity of the user.

Figure 7C:
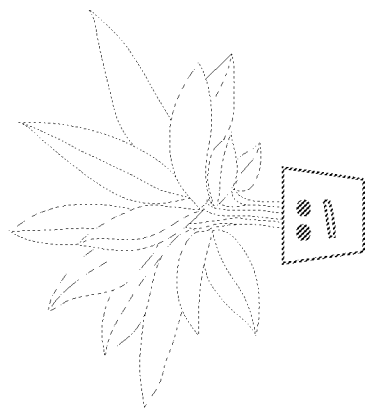
FIGS. 7A-7C depict several example visual representations of a virtual sidekick.
Figure 7B:
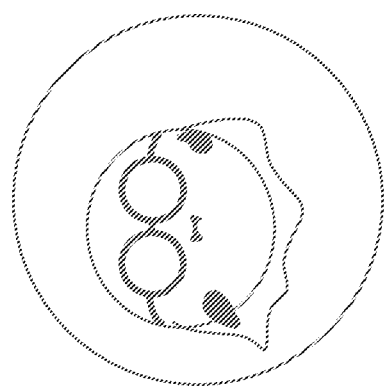
Figure 7A:
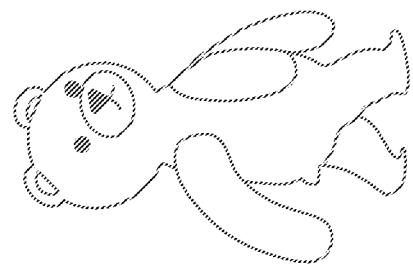

As previously discussed, a virtual sidekick may be depicted as an animated character such as the stylized bear shown in FIG. 5; however, this is not intended to be limiting. The virtual sidekick may be depicted differently in other embodiments. For example, FIGS. 7A, 7B, and 7C depict example virtual sidekicks in the form of a stylized bear, a stylized anthropomorphized ball, and a stylized anthropomorphized plant. Again, these are examples, and not to be construed as limiting. Other embodiments may depict the virtual sidekick as a human, some other animal, or some other object. In some embodiments, instead of depicting the virtual sidekick as an animated stylized character, the virtual sidekick may be depicted as a realistic human character, as a realistic animal, or as some other realistic object. In some embodiments, the virtual sidekick may be depicted as an avatar of the user. In such embodiments, the virtual sidekick may share certain visual attributes of the user such as similar clothes, similar facial features, similar hair, etc. In short, the virtual sidekick may take any visual form.

In some embodiments, the user may be provided with an option to select from multiple pre-configured visual representations of a virtual sidekick. For example, each of the example virtual sidekicks shown at FIGS. 7A-7C may be presented, via the GUI, as an option to the user. In some embodiments, users may access customized visual representations of virtual sidekicks that are created by third parties such as other users of the health management platform 102. In some embodiments, the health management platform 102 may automatically select a visual representation of a virtual sidekick for the user, for example, based on various input data such as an age of the user, a gender of the user, a chronic health condition of the user, a location of the user, a personality type of the user, etc. For example, the health management platform 102 may analyze interaction data associated with the user (e.g., based on interaction with health management platform 102 or other communication channels), determine a personality type associated with the user based on the analysis, and select a particular visual representation for the virtual sidekick based on the personality type.

Figure 8C:
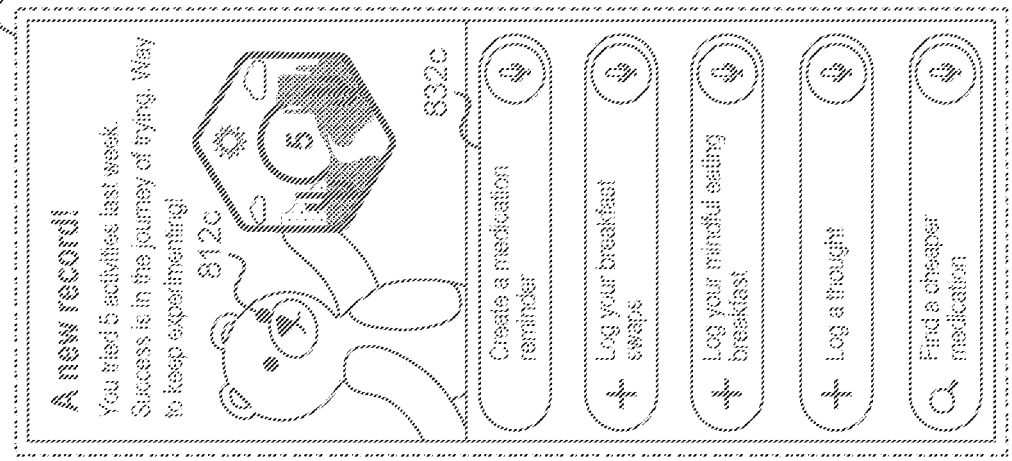
FIGS. 8A-8C show a series of example states of an example graphical user interface of a health management platform that illustrate how a visual representation of a virtual sidekick may be dynamically updated.
Figure 8B:
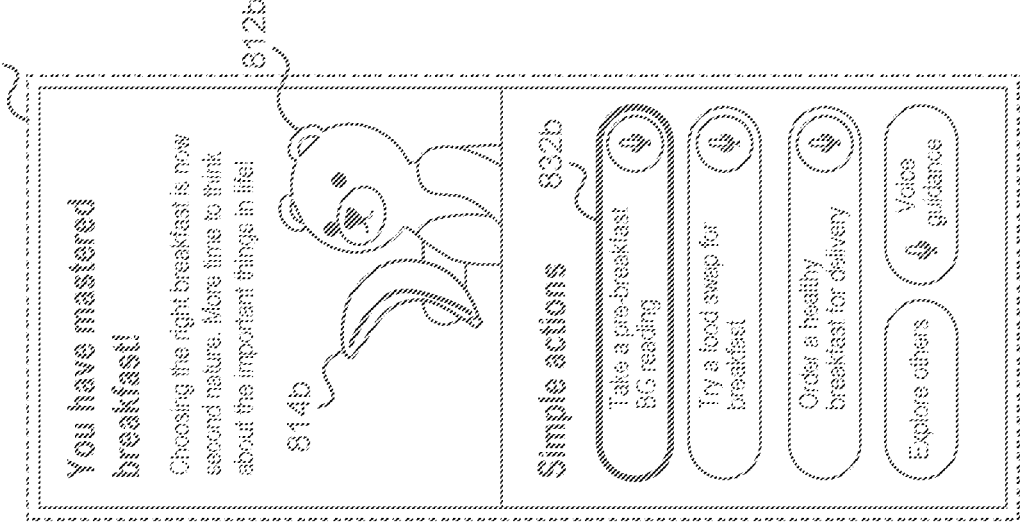
Figure 8A:
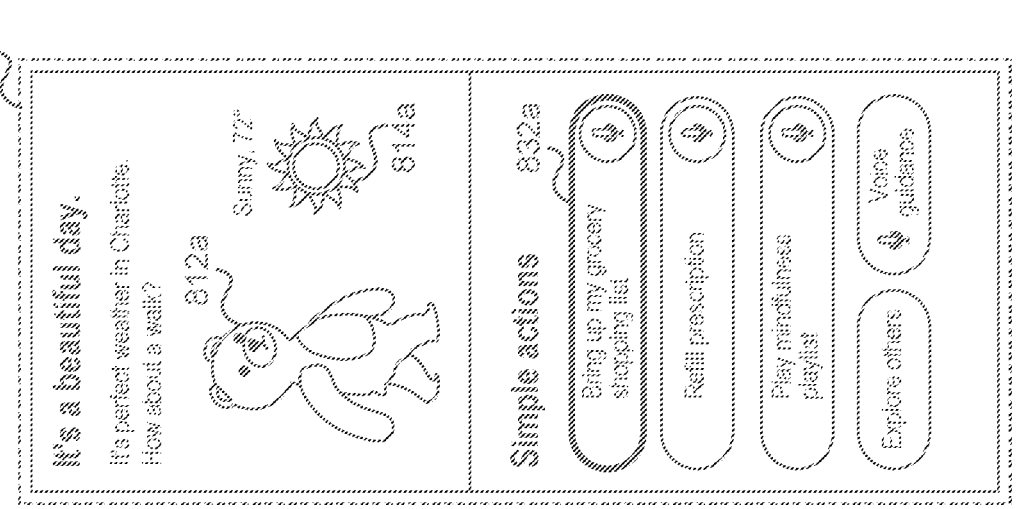

As updated input data are received by the health management platform 102 (e.g., via pipeline 400), the visual representation of the virtual sidekick may be dynamically updated, changed, or otherwise adjusted. For example, the visual representation of the virtual sidekick may be dynamically updated, changed, or otherwise adjusted based on a health state of the user, a mood of the user, an activity performed by the user, etc. FIGS. 8A-8C shows a series of example states 800*a-c* (respectively) of a GUI that illustrate how a visual representation of the virtual sidekick may be dynamically updated, changed, or otherwise adjusted.

FIG. 8A shows a first state 800*a* of the example GUI that generally corresponds with the example GUI 500 depicted in FIG. 5. As shown in FIG. 8A, a first state of the virtual sidekick 812a is depicted as walking and is displayed next to a visual representation of a reverse augmented reality element in the form of a stylized sun 814a that is representative of the sunny weather at the user's physical location in Charlotte. The first state of the virtual sidekick 812a may be depicted as shown in FIG. 8A based, for example, on fitness tracking data received indicating that the user is currently walking, on physiological data received indicating that a health state of the user may be improved by going for a walk, on weather data indicating weather at the user's physical location that is conducive for a walk, or any combination thereof.

FIG. 8B shows a second state 800b of the example GUI. As shown in FIG. 8B, a second state of the virtual sidekick 812b is depicted as holding a reverse augmented reality element in the form of a stylized banana 814b that is representative of completed or in-progress meal swap challenge. The second state of the virtual sidekick 812b may be depicted as shown in FIG. 8B based, for example, on a user input via the GUI indicating that the user is attempting or completed a meal swap challenged, on a picture of a meal uploaded by the user as part of a meal swap challenge, on physiological data received indicating that a health state of the user may be improved by swapping a food item in a meal for a healthier option such as a banana, or any combination thereof.

FIG. 8C shows a third state 800c of the example GUI. As shown in FIG. C, a third state of the virtual sidekick 812c is depicted as celebrating the user's new record for trying new activities in the past week. The third state of the virtual sidekick 812c may be depicted as shown in FIG. 8C based, for example, on a user input via the GUI indicating that the user has tried a new activity recently, tracked fitness activity data for the user over a given time period such as a week, on tracked user interaction with various features of the health management platform 102, or an combination thereof.

Notably, in some embodiments, other interactive elements in the GUI may also be dynamically updated, changed, or otherwise adjusted as updated input data are received via the data pipeline 400. For example, FIG. 8A shows a first state 800a of the example GUI that includes a first set of interactive elements 832a. In the example depicted in FIG. 8A, the first set of interactive elements 832a include options for the user to perform quick actions such as bringing up a shopping list, refilling a prescription, and playing a mindfulness playlist. FIG. 8B shows a second state 800b of the example GUI that includes a second set of interactive elements 832b. In the example depicted in FIG. 8B, the second set of interactive elements 832b include options for the user to perform quick actions such as taking a pre-breakfast blood glucose reading, trying a food swap for breakfast, and ordering a health breakfast for delivery. FIG. 8C shows a third state 800c of the example GUI that includes a third set of interactive elements 832c. In the example depicted in FIG. 8C, the third set of interactive elements 832c include options for the user to perform quick actions such as creating a medication reminder, logging a breakfast swap, logging a thought, etc.

In some embodiments, the depicted interactive elements may dynamically change to correspond with recommendations or other actions by the virtual sidekick. For example, in the first state of 800a of the GUI, a first state of the virtual sidekick 812a is depicted as walking indicating, for example, that the system has detected the user walking or that the system is recommending that the user take a walk. The displayed first set of interactive elements 832a may correspond to the walking activity. For example, the user may take advantage of the walk to go grocery shopping. Accordingly, the first set of interactive elements may include an option to bring up grocery shopping list. As another example, the user may take advantage of the walk to visit a pharmacy to refill a prescription. Accordingly, the first set of interactive elements may include an option to submit an order to the pharmacy to refill the prescription. As another example, the health state of the user may be further benefited by remaining mindful during the walk. Accordingly, the first set of interactive elements may include an option to play a mindfulness playlist, for example, via a music streaming service such as Spotify™.

As the visual representation of the virtual sidekick changes from the first state 812a to the second state 812b, certain interactive elements may similarly change to correspond with the change. For example, in the second state 800b of the GUI, a second state of the virtual sidekick 812b is depicted as holding a reverse augmented reality element in the form of a stylized banana 814b that is representative of completed or in-progress food swap challenge. Accordingly, the displayed second set of interactive elements 832b may correspond to the food swap challenge. For example, as part of a food swap challenge, a diabetic user may take blood glucose readings to track how the user's blood glucose levels respond when swapping one food item (e.g., a donut) for another food item (e.g., a banana). Accordingly, the second set of interactive elements 832b may include an option to take a pre-meal blood glucose reading (e.g., using a connected blood glucose meter). As another example, the user may need assistance obtaining a food item as part of a food swap challenge. Accordingly, the second set of interactive elements 832b may include an option to order a health breakfast for delivery, for example, using an online meal delivery service.

Figure 9:
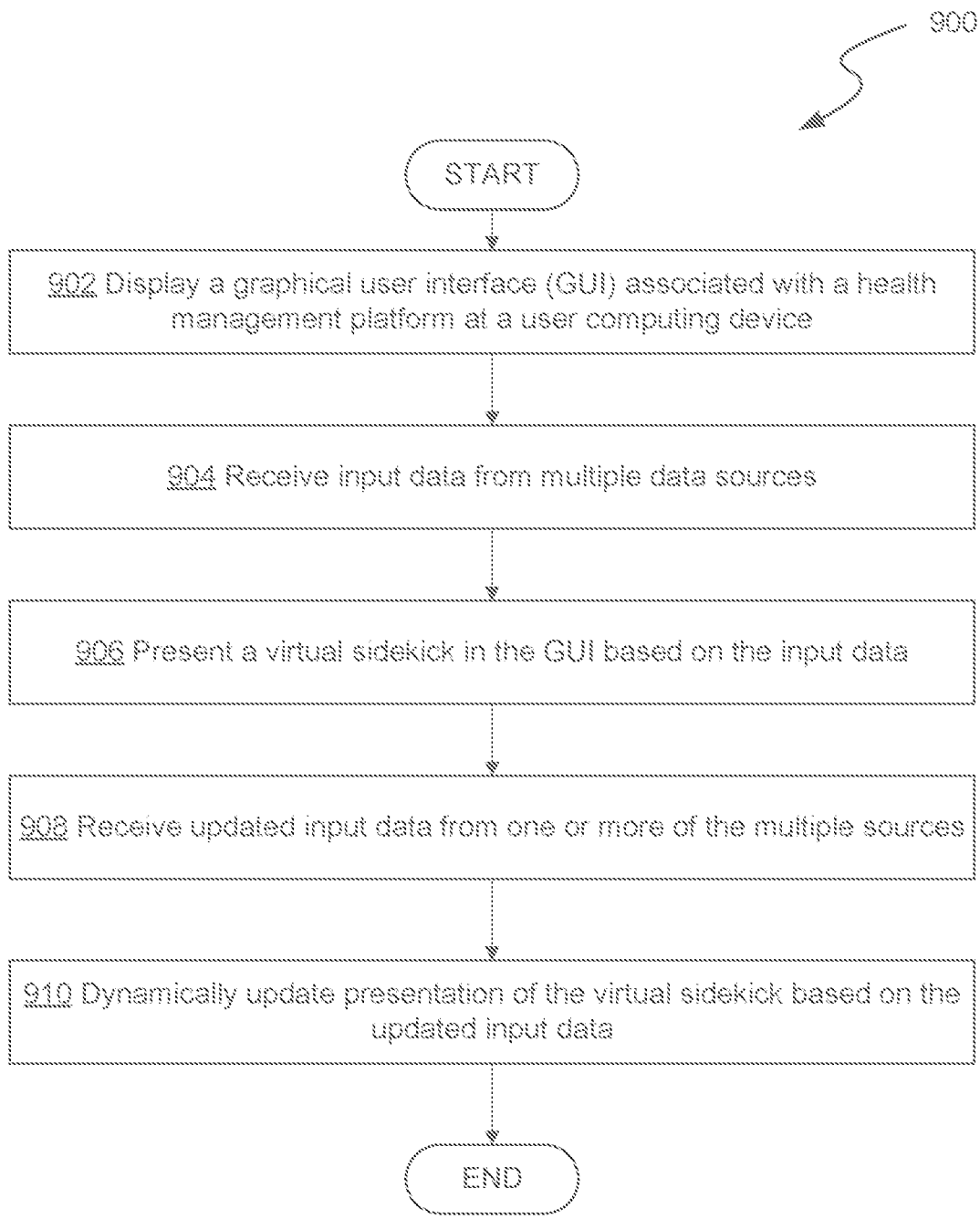
FIG. 9 shows a flow diagram of an example process for presenting a virtual sidekick.

FIG. 9 shows a flow diagram of an example process 900 for presenting a virtual sidekick, according to an embodiment of the introduced technique.

Example process 900 begins at operation 902 with displaying a GUI associated with a health management platform at a user computing device. For example, as described with respect to FIG. 1, an individual user (e.g., a patient with a chronic health condition) may access various functionalities of a health management platform 102 using interface 104. Interface 104 may include a GUI that is displayed at a user computing device using any type of application configured to present a GUI.

Example process 900 continues at operation 904 with receiving input data from multiple different data sources. For example, as described with respect to FIG. 4, various input data may be received by one or more computer systems associated with a health management platform 102 via a data pipeline 400. The input data may include, for example, user inputs via the GUI presented at operation 902, location data received from the user computing device, weather data received from a weather service, social media data received from one or more social media platforms, physiological data received from a health monitoring device, fitness data received from a fitness tracking device, IOT data received from various network connected devices around the user's home, and various other types of data.

Example process 900 continues at operation 906 with presenting a virtual sidekick in the GUI based on the input data. As previously discussed with respect to FIG. 5, the virtual sidekick presented via the GUI may be configured to assist a user in managing a chronic health condition such as diabetes. In some embodiments, operation 906 may include displaying a visual representation of the virtual sidekick, for example, as depicted in FIG. 5. In some embodiments, the visual representation of the virtual sidekick may include an animated character such as the animated stylized bear 512 depicted in FIG. 5, although other types of characters or objects may be similarly implemented. In some embodiments, operation 906 may include displaying a visual representation of the virtual sidekick in a virtual scene that includes one or more reverse augmented reality elements that are indicative of a physical context of the user such as a physical location of the user, the weather at the physical location of the user, an object in proximity to the user, or an activity performed by the user. For example, as described with respect to FIG. 5, a visual representation of a virtual sidekick 512 may be displayed in a virtual scene in the GUI along with a visual representation of a reverse augmented reality element 514. In some embodiments, presentation of the virtual sidekick in the GUI may additionally include non-visual elements such as audible outputs. For example, operation 906 may include causing a speaker at the user computing device to output sounds associated with the virtual sidekick (e.g., speech, non-verbal audible expressions, other sound effects). Various ways in which the input data may be used to present the virtual sidekick are described in greater detail later.

Example process 900 continues at operation 908 with receiving updated input data from one or more of the multiple data sources. For example, as previously discussed with respect to FIG. 4, in some embodiments, input data may be received by the health management platform 102 from one or more data sources, continually or on a periodic basis (e.g., hourly, daily, weekly) via the data pipeline 400. Depending on the data source, input data may be passively received by the health management platform 102 (continually or on a period basis) and/or actively pulled (continually or on a period basis). For example, the health management platform 102 may passively receive updated physiological data (continually or on a period basis) based on uploads from a communicatively coupled health monitoring device. The same health management platform 102 may actively pull updated location data (continually or on a period basis) from the user's computing device.

Example process 900 concludes with dynamically updating presentation of the virtual sidekick based on updated input data received at operation 908. In some embodiments, dynamically updating presentation of the virtual sidekick may include changing the depiction of a visual representation of the virtual sidekick in the GUI. For example, based on updated input data, a visual depiction of the virtual sidekick may change from a first state (e.g., the first state 812*a* in FIG. 8A) to a second state (e.g., the second state 812*b* in FIG. 8B). Similarly, based on updated input data, a visual depiction of a reverse augmented reality element may change from a first state (e.g., the first state 814*a* in FIG. 8A) to a second state (e.g., the second state 814*b* in FIG. 8B).

In this context, dynamically changing the presentation of the virtual sidekick may include changing the visual depiction of the virtual sidekick automatically with or without any direct input from the user of the user computing device. For example, with or without any direct interaction by the user with GUI, the visual depiction of the virtual sidekick may dynamically change from a first state (e.g., the first state 812*a* in FIG. 8A) to a second state (e.g., the second state 812*b* in FIG. 8B).

As an illustrative example, updated fitness data may indicate that the user's activity state has changed from an inactive state to an active state. The visual representation of the virtual sidekick can accordingly be dynamically updated to reflect or respond to that change in activity state. For example, if the user was previously inactive and is now exercising (as indicated in the updated fitness data), the visual representation of the virtual sidekick may dynamically change to mirror the user's activity (e.g., through displaying an animation of the virtual sidekick running) or may dynamically change to respond to the user's activity (e.g., through displaying an animation of the virtual sidekick cheering the user on or giving a thumbs up).

As another illustrative example, updated weather data may indicate that the weather at the user's physical location has changed from sunny to cloudy. The visual representations of virtual sidekick and/or a reverse augmented reality element can accordingly be dynamically updated to reflect or respond to the change. For example, the reverse augmented reality element indicative of sunny weather (e.g., the stylized sun 814*a* shown in FIG. 8A) may dynamically change into a reverse augmented reality element indicative of the cloudy weather (e.g., a stylized image of a cloud). Further, the visual representation of the virtual sidekick may dynamically change to reflect or respond to the change in weather (e.g., through displaying an animation of the virtual sidekick putting on a jacket or shivering).

In some embodiments, dynamically updating presentation over the virtual sidekick (and other virtual scene elements) may include displaying several different transitional states to produce a smooth transition from a first state to a second state. For example, if a first state of the visual representation of the virtual sidekick depicts the virtual sidekick sitting (e.g., to reflect the user sitting) and a second state of the visual representation of the virtual sidekick depicts the virtual sidekick running (e.g., to reflect the user running), dynamically changing between the first state and the second state may include displaying transitional animations that depict the virtual sidekick standing up from a sitting position, stretching, walking out a door, etc.

Figure 10:
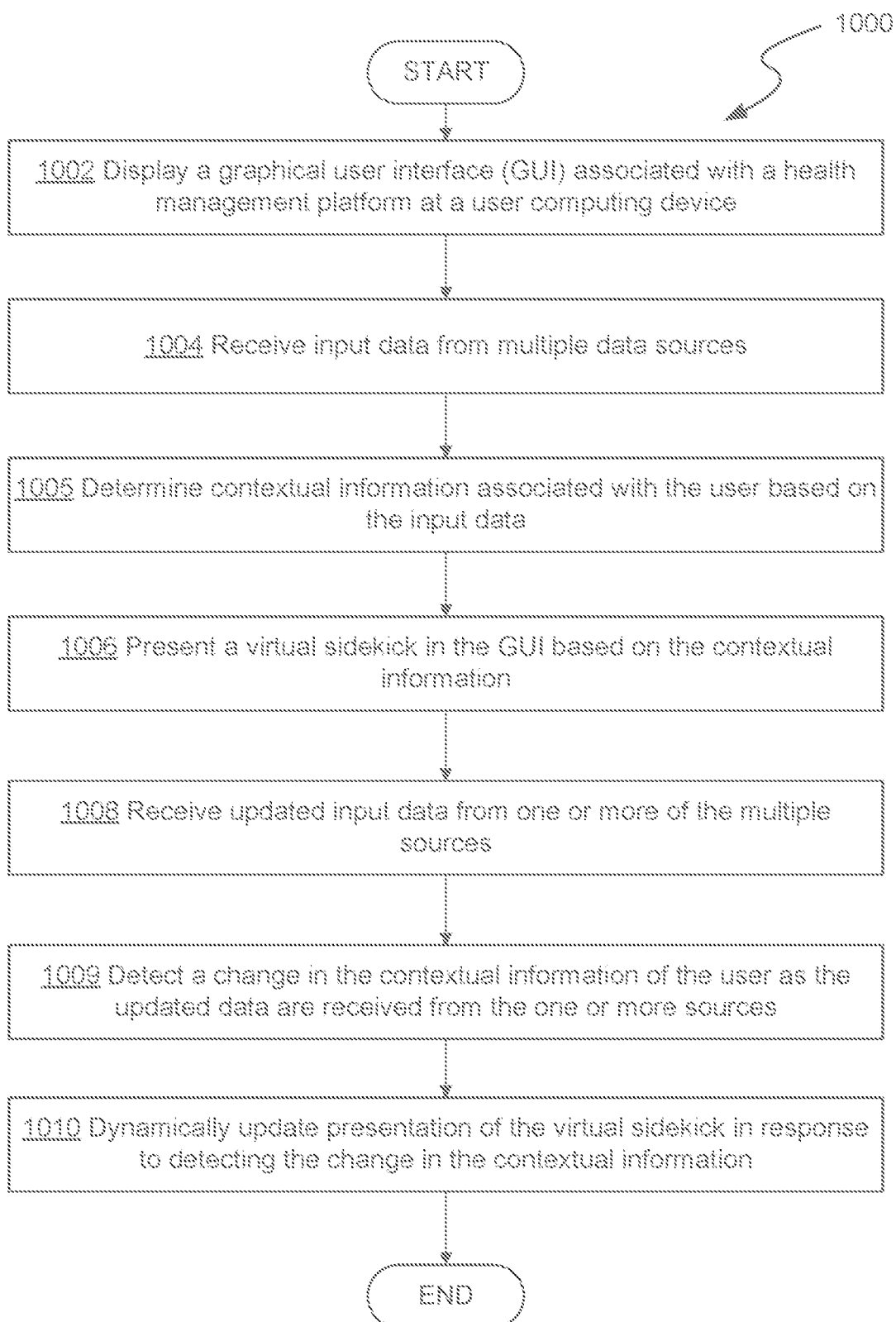
FIG. 10 shows a flow diagram of another example process for presenting a virtual sidekick.

In some embodiments, input data received by the health management platform 102 may be processed to determine contextual information associated with the user. This contextual information can then be used to inform the presentation of the virtual sidekick in the GUI. FIG. 10 shows a flow diagram of another example process 1000 for presenting a virtual sidekick that is similar to example process 900, but includes the additional operation of determining contextual information associated with the user.

Example process 1000 begins at operations 1002 and 1004 with displaying a GUI associated with a health management platform and receiving input data from multiple different data sources, for example, as described with respect to operations 902 and 904 of example process 900.

Example process 1000 continues at operation 1005 with determining contextual information associated with the user based on the input data. In other words, operation 1005 may include processing raw input data received from the multiple data sources to learn, infer, identify, or otherwise determine some type of understanding of the context of the user. Contextual information may include, for example, information indicative of the chronic health condition of the user (e.g., diabetes, arthritis, etc.), a physical health state of the user, a mood of the user (happy, sad, etc.), an activity performed by the user (e.g., sitting, running etc.), a physical location of the user (e.g., in Charlotte, at home, etc.), a weather condition at a physical location of the user (e.g., sunny, raining, etc.), or any other type of information that provides context regarding the user.

In some embodiments, operation 1005 may include processing input data received at operation 1004 to determine a chronic health condition (e.g., diabetes) of the user. Input data used to determine the chronic health condition of the user may include, for example, user survey data input by the user via the GUI, data received from the user's physician, etc.

Determining a chronic health condition of a user is important in certain embodiments since such information can be used to specifically tailor the presentation of a virtual sidekick to the user. For example, the chronic health condition of the user may impact which computer program is used to simulate the virtual sidekick, what types of health interventions are encouraged by the virtual sidekick, how the virtual sidekick is visually depicted, and how the virtual sidekick responds to actions by the user.

As an illustrative example, the virtual sidekick can be depicted as facing the same or similar challenges as the user to encourage a peer relationship with the user. For example, if the user has diabetes, a visual representation of the virtual sidekick can be configured to convey that the virtual sidekick has diabetes or a similar condition. Visual representation of the virtual sidekick can be configured to convey such information in many different ways. In the illustrative case of diabetes, the virtual sidekick may be animated to self-administer a glucose measurement using a glucose monitoring device or self-administer medication such as insulin.

As another illustrative example, information associated with the chronic health condition of the user may be used to select a particular computer program to simulate the virtual sidekick. For example, the health management platform 102 may include multiple condition-specific computer programs that each include separate instructions for simulating a virtual sidekick to assist a user in managing a respective chronic health condition. In response to determining the chronic health condition of the user, the health management platform 102 may select a particular condition-specific computer program from a repository of multiple condition-specific computer programs and use the selected condition-specific computer program to simulate the virtual sidekick.

In some embodiments, operation 1005 may include processing input data received at operation 1004 to determine a health state of the user. The term "health state" can refer to physical health, mental health, emotional health, or any combination thereof. Input data used to determine the physical and/or mental health state of the user may include, for example, user inputs received via the GUI, physiological data received from a health monitoring device, fitness data received from a fitness tracking device, social media data including posts by the user, etc.

As an illustrative example, a physical health state for a diabetic user may include a glycemic state determined based on measured blood glucose levels received from a glucose monitoring device. In such an example, the health state may be defined categorically (e.g. low, normal, high, etc.) or in any other appropriate manner.

As another illustrative example, a mental or emotional state for a user may be determined by analyzing sensor inputs from a camera and/or microphone of the user computing device. For example, images of the user captured by a camera may be analyzed to identify features indicative of a defined mental or emotional state. Similarly, recordings of the user's voice captured by a microphone may be analyzed to identify features indicative of a defined mental or emotional state. Identified features used to determine a health state of the user may include linguistic features, non-linguistic features, and/or paralinguistic features. Linguistic features refer to aspects of spoken communication that involve words. Examples of linguistic features include the word count of different n-grams, whether jargon/slang is used, etc. Paralinguistic features refer to those aspects of communication that do not involve speech. Paralinguistic features often add emphasis or shades of meaning to what an individual says. Examples of paralinguistic features may include body language, gestures, facial expressions, micro expressions, etc. Non-linguistic features also refer to those aspects of spoken communication that do not involve words. Much like paralinguistic features, non-linguistic features can add emphasis or shades of meaning to what an individual says. Examples of non-linguistic features include tone, pitch, volume/loudness, speaking rate, shimmer, jitter, etc.

Determining a health condition of the user is important in certain embodiments since such information can be used to dynamically update presentation of the virtual sidekick to respond to the health condition of the user. For example, the health state of the user may impact what types of health interventions are encouraged by the virtual sidekick, how the virtual sidekick is visually depicted, and how the virtual sidekick responds to actions by the user. For example, a detected health state of the user may be used to determine whether the user is effectively managing their chronic health condition, whether the user has reached a milestone associated with a health goal, etc. With such information, the presentation of the virtual sidekick can be dynamically updated to, for example, encourage a new behavior by the user that will improve their health state and/or encourage continued behavior by the user that will improve their health state. In some embodiments, operation 1005 may include processing input data received at operation 1004 to determine an activity by the user. An activity of the user may be determined by analyzing sensor inputs from any number of device such as a user computing device and/or a fitness tracking device. For example, operation 1005 may include analyzing images from a camera, motion data from an accelerometer, heart rate data from a heart rate sensor, or any combination thereof to detect motion by the user and or a level of physical exertion and thereby infer or otherwise determine a type of activity performed by the user (e.g., standing still, walking, running, jumping, etc.). In some embodiments, the input data may be processed in real-time or near-real-time (i.e., within seconds or fractions of a second) to determine an activity currently being performed by the user.

Determining an activity of the user is important in certain embodiments since such information can be used to dynamically update presentation of the virtual sidekick to respond to the user's activity. Dynamically updating the virtual sidekick in response to detected user activity can help encourage interaction between the user and the virtual sidekick which may improve the effectiveness of health interventions encouraged through the use of the virtual sidekick.

In some embodiments, operation 1005 may include processing input data received at operation 1004 to determine a physical location of the user. A physical location of the user may be determined by analyzing location data, for example, received from the user computing device. For example, the user computing device may transmit GPS coordinates to a computer system of the health management platform 102. Location data (e.g., in the form of GPS coordinates) may be used to identify a physical locale or landmark corresponding to the user's exact physical location. For example, using received GPS coordinates, the system may determine that the user is in a particular city (e.g., Charlotte), in a particular neighborhood, at a particular physical address, at a particular type of location (e.g., at home, a gym, or a doctor's office), etc.

Determining a physical location of the user is important in certain embodiments since such information can be used to configure the presentation of the virtual sidekick and/or any reverse augmented reality elements presented with the virtual sidekick. For example, a reverse augmented reality element can be generated based on the user's physical location and presented with a virtual sidekick to instill, in the user, a sense of proximity to the virtual sidekick. This sense of proximity to the virtual sidekick can, for example, promote a peer relationship between the user and the virtual sidekick thereby encouraging engagement between the user and the virtual sidekick.

In some embodiments, operation 1005 may include processing input data received at operation 1004 to determine a weather condition at a user's physical location. The weather condition at the physical location of the user may be determined by analyzing location data of the user and cross referencing to weather data from an online weather service. For example, in response to receiving location data (e.g., in the form or GPS coordinates), the system may access an online weather service to determine a weather condition (e.g., sunny, raining, etc.) at a physical location corresponding the received location data.

Determining a weather condition at a physical location of the user is important in certain embodiments since such information can be used to configure the presentation of the virtual sidekick and/or any reverse augmented reality elements presented with the virtual sidekick. For example, a reverse augmented reality element can be generated based on a weather condition at a user's physical location and presented with a virtual sidekick to instill, in the user, a sense of proximity to the virtual sidekick. As with reverse augmented reality elements indicative of a physical location, a reverse augmented reality element indicative of a weather condition at the physical location may instill, in the user, a sense of proximity to the virtual sidekick. Further, information regarding a weather condition at the user's physical may dictate what types of interventions are presented, by the virtual sidekick, to the user. For example, if the weather is sunny, a visual representation of the virtual sidekick may be configured to depict the virtual sidekick performing an outdoor exercise activity thereby indirectly encouraging the user to go outdoors and perform a similar exercise activity.

In some embodiments, operation 1005 may include processing received input data using one or more rules to determine the contextual information associated with the user. For example, a rule may specify that a user's location is at home if received GPS coordinates are within a threshold distance of a user's known home address. As another example, a rule may specify that a user's physical health state is normal if blood glucose levels received from a glucose monitoring device are within a predefined range. These are just some illustrative examples of rules that may be applied to determine contextual information based on received input data.

In some embodiments, operation 1005 may include processing received input data using one or more machine learning models to determine the contextual information associated with the user. For example, a machine learning model may be trained to infer a physical health state of a user based on input physiological data. As another example, a machine learning model may be trained to infer an activity performed by a user based on input motion data and physiological data. In any case, the one or more machine learning models may apply one or more different processes to the data using various machine learning techniques such as decision trees, Naïve Bayes classifiers, support vector machines, random forests, artificial neural networks, etc.

Example process 1000 continues at operation 1006 with presenting a virtual sidekick in the GUI, for example, similar to as described with respect to operation 906 of example process 900.

Example process 1000 continues at operation 1008 with receiving updated input data, for example, similar to as described with respect to operation 908 of example process 900.

Example process 1000 continues at operation 1009 with detecting a change in the contextual information of the user based on the updated input data received at operation 1008. For example, as updated location data are received, operation 1009 may include detecting that a user has moved from a first location to a second location. As another example, as updated physiological data are received, operation 1009 may include detecting that a user's health state has changed from a first health state (e.g., healthy) to a second health state (e.g., sick).

Example process 1000 concludes at operation 1010 with dynamically updating presentation of the virtual sidekick in response to detecting the change in the contextual information associated with the user. For example, in response to detecting a change in the emotional state of the user (e.g., from happy to sad), operation 1010 may include dynamically updating display of the virtual sidekick to depict the emotional state of the virtual sidekick changing to mirror the user (i.e., from happy to sad) or to respond to the change in the user's emotional state (e.g., from happy to empathetic to encourage the user).

As previously alluded to, in some embodiments, the presentation of the virtual sidekick in the GUI may be based on a health state of the user that is determined based on various input data. For example, in such embodiments, operation 1005 of example process 1000 may include determining a physical, mental, and/or emotional health state of the user based on input data and operation 1006 may include presenting the virtual sidekick in the GUI so as to include a visual representation of the virtual sidekick based on the health state of the user.

In some embodiments, the visual representation of the virtual sidekick may correspond to the health state of the user by mirroring the health state of the user. If the system determines that the user is feeling physically ill, the visual representation of the virtual sidekick may be configured to indicate that the virtual sidekick is also feeling physically ill, for example, by causing an expression of the virtual sidekick to indicate a poor physical health state, causing the virtual sidekick to make gestures or motions that indicate a poor physical health state, changing the color of the virtual sidekick to indicate a poor physical health state, or adding other visual elements such as a thermometer or bandage. In some embodiments, visual indicators by the virtual sidekick may not necessarily correspond to actual visual indicators of the user's medical condition. For example, certain chronic health conditions may be associated with health states of symptoms that are not readily conveyed through visual indicators. As an illustrative example, if a user has diabetes and is experiencing nausea, a color of the virtual sidekick may be changed to green to indicate the nausea even though the user is not actually turning green.

Figure 11:
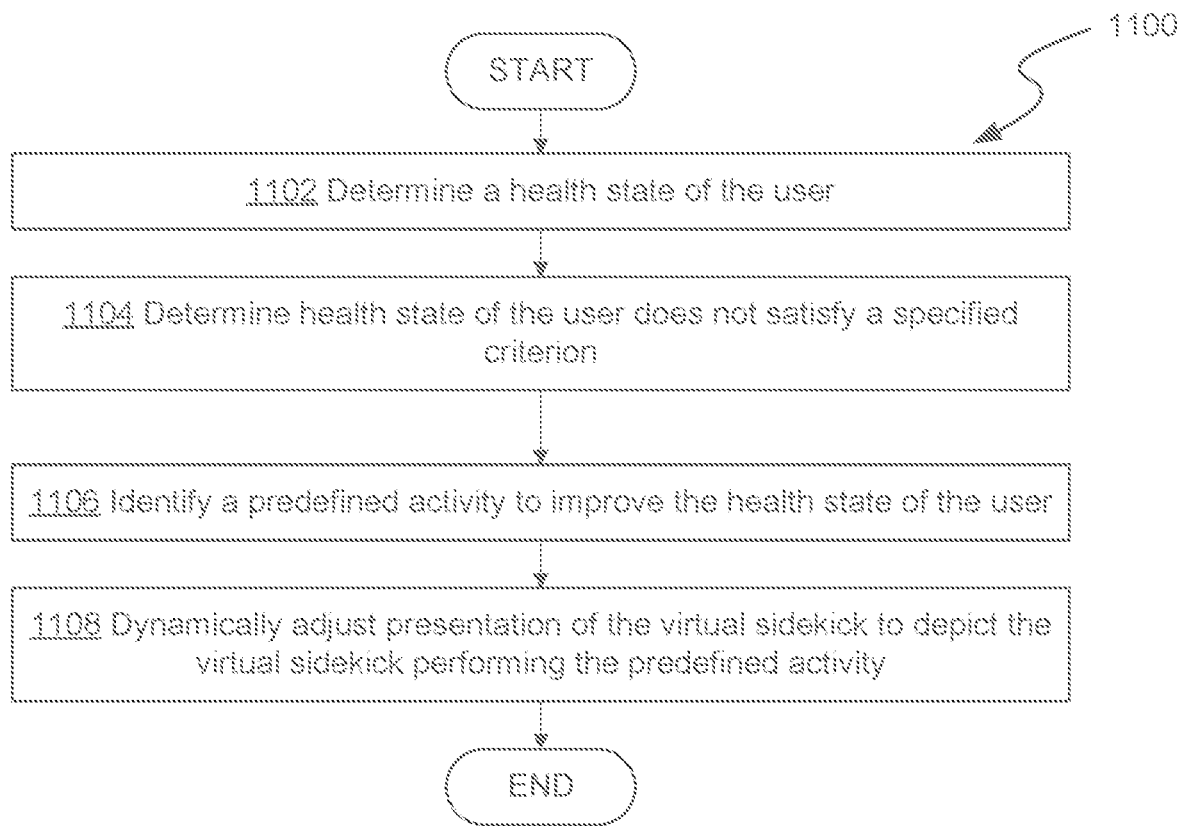
FIG. 11 shows a flow diagram of an example process for depicting the virtual sidekick performing an activity to improve a health state of a user.

In some embodiments, the visual representation of the virtual sidekick may correspond to the health state of the user by instead responding to the health state of the user. For example, in some embodiments, a virtual sidekick may offer encouragement to improve the health state of the user by demonstrating an activity that is known or likely to improve the health state of the user. FIG. 11 shows a flow diagram of an example process 1100 for depicting the virtual sidekick performing an activity to improve a health state of a user.

Example process 1100 begins at operation 1102 with determining a health state of a user based on input data, for example, as described with respect to operation 1005 of example process 1000.

Example process 1100 continues at operation 1104 with determining that the health state of the user does not satisfy a specified criterion, thereby indicating measures should be taken to improve the health state of the user. In some embodiments, determining whether the health state of the user satisfies a specified criterion may include determining whether a quantified measure indicative of the health state meets or exceeds a threshold value or is within a specified range. For example, a health state of the user may be indicated by a quantified measure such as blood glucose level. In such an example, the health state of the user may satisfy a specified criterion if the blood glucose level is within a specified normal range. If the blood glucose level is outside the range (i.e., above a maximum value or below a minimum value), then the specified criterion is not satisfied, and measures may need to be taken to improve the health state of the user.

Example process 1100 continues at operation 1106 with identifying a predefined activity that is known or likely to improve the health state of the user in response to determining that the health state of the user does not satisfy the specified criterion. The type of predefined activity will differ depending on the type of health state of the user and the type of chronic health condition of the user. Examples of predefined activities that may improve the health state of the user include, using a health monitoring device to acquire updated physiological data, performing a fitness activity (i.e., exercising), performing a food swap activity (i.e., swapping a food item for a healthier alternative), consulting a health expert (e.g., calling or visiting a doctor), taking a medication, performing a mindfulness activity (e.g., meditating), etc.

In some embodiments, one or more rules may be applied to identify an activity that will improve a health state of the user. For example, various data indicative of the health state of the user may be processed using one or more rules to select a particular predefined activity (e.g., exercise) from a database of multiple predefined activities. In some embodiments, one or more machine learning models may be applied to identify an activity. For example, the various data indicative of the user's health state may be fed into one or more trained machine learning models to generate an output indicating a selection of a particular predefined activity (e.g., exercise) from a database of multiple predefined activities.

Example process 1100 concludes at operation 1108 with dynamically adjusting a visual representation of the virtual sidekick in the GUI to depict the virtual sidekick performing or attempting to perform the predefined activity identified at operation 1106. For example, if the health state of the user is likely to be improved through an exercise activity such as a walk, operation 1108 may include depicting the virtual sidekick taking a walk, for example, as depicted in FIG. 8A. As another example, if the health state of the user is likely to be improved through adjusting diet, operation 1108 may include depicting the virtual sidekick swapping a food item for meal (e.g., a muffin during breakfast) for a healthier option such as a banana, for example, as depicted in FIG. 8B.

Depicting the virtual sidekick performing, or attempting to perform, the predefined activity identified at operation 1106 provides indirect encouragement to a user to perform the same activity or a substantially similar activity. In some situations, such indirect encouragement may be more effective at encouraging a behavioral change on the part of the user than a direct recommendation or order from a health care professional. In addition to encouraging the user, the depiction of the virtual sidekick may provide a non-verbal instruction on how to perform the predefined activity. For example, if the predefined activity identified at operation 1106 is a particular exercise activity, a depiction of the virtual sidekick performing, or attempting to perform, the particular exercise activity can provide a visual instruction to the user on how to perform the particular exercise activity.

As previously discussed, in some embodiments, a virtual sidekick may be configured to be fallible to make the virtual sidekick more relatable to the user. In such embodiments, operation 1108 may include dynamically adjusting the visual representation of the virtual sidekick to depict the virtual sidekick making a mistake while performing or attempting to perform the predefined activity identified at operation 1106. For example, if the identified activity is using a health monitoring device to acquire updated physiological data, operation 1108 may include dynamically adjusting the visual representation of the virtual sidekick to depict the virtual sidekick using the health monitoring device incorrectly or otherwise making a mistake taking the measurement. In some embodiments, this mistake may be followed up by causing the virtual sidekick to seek help from the user to correct the mistake. By doing so, the user may be incentivized to identify mistakes made by the virtual sidekick which, in turn, may help the user to avoid similar mistakes when performing similar activities to manage the user's own health condition.

In some embodiments, operation 1108 may additionally include dynamically adjusting a virtual scene in which the virtual sidekick is presented to include a reverse augmented reality element associated with the activity identified at operation 1106. For example, if the activity identified at operation 1106 is associated with a physical object, operation 1108 may include presenting an augmented reality element indicative of the physical object in the virtual scene along with the visual depiction of the virtual sidekick. As an illustrative example, if the predefined activity is an exercise activity (e.g., lifting weights), the physical object associated with that activity may include a dumbbell. In such an embodiment, a reverse augmented reality element indicative of a dumbbell may be displayed along with the visual depiction of the virtual sidekick. As another illustrative example, if the predefined activity is a food swap activity, the physical object associated with that activity may include a food item such as a banana. In such an embodiment, a reverse augmented reality element indicative of the banana may be displayed along with the visual depiction of the virtual sidekick, for example, as shown in FIG. 8B. As another illustrative example, if the predefined activity is a health measurement activity (e.g., taking a blood glucose reading), the physical object associated with that activity may include a health monitoring device used to perform the health measurement activity. In such an embodiment, a reverse augmented reality element indicative of the health measurement device (e.g., a blood glucose monitor) may be displayed along with the visual depiction of the virtual sidekick.

Figure 12:
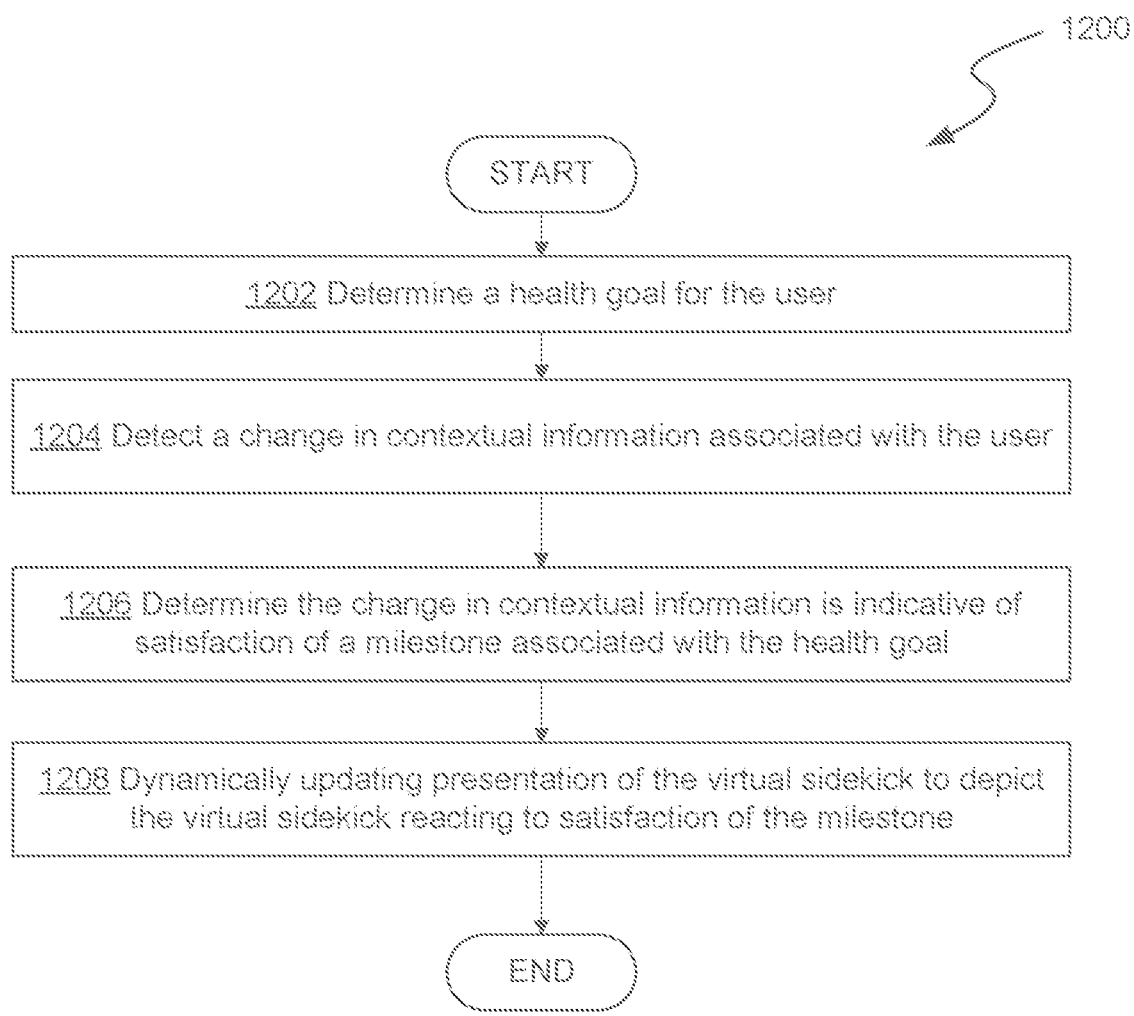
FIG. 12 shows a flow diagram of an example process for using a virtual sidekick to encourage a user to meet a health goal.

In some embodiments, the virtual sidekick may assist the user in managing his or her chronic health condition by providing encouragement to the user to complete one or more health goals configured to improve the overall health of the individual. FIG. 12 shows a flow diagram of an example process 1200 for using a virtual sidekick to encourage a user to meet a health goal.

Example process 1200 begins at operation 1202 with determining a health goal for the user. A "health goal" in this context may include, for example, one or more predefined milestones related to the user's health state and/or activities to improve the user's health state. For example, if the user is diabetic, a health goal may include maintaining a blood glucose level within a particular healthy range. As another example, a health goal may include walking at least a particular number of steps each day.

In some embodiments, the health goal for the user may be based on input data received by the health management platform 102, for example, as described with respect to operation 904 of example process 900.

In some embodiments, input data may indicate a selection by the user, via the GUI, of a particular predefined health goal challenged from multiple predefined health goal challenges offered by the health management platform 102. For example, a health management platform 102 may present, via the GUI, an option to take a health challenge such as an exercise challenge or a food swap challenge that is associated with certain health goals. As an illustrative example, a health goal associated with an exercise challenge may include walking a certain number of steps each day for week.

In some embodiments, input data received from a computing device associated with a health coach or physician may indicate that the health coach or physician has set a particular health goal for the user. For example, the health management platform may be configured to allow a second user (e.g., a health coach or physician) to monitor various physiological or fitness data associated with a first user that has the chronic health condition. Using his or her expertise, the second user may recommend or set certain health goals for the first user that are intended to improve the health of the first user.

In some embodiments, input data and/or contextual information may be processed by a computer system associated with the health management platform 102 to configure automatically a health goal for the user to improve the health of the user. For example, a computer system associated with the health management platform 102 may parse physiological data (e.g., measured blood glucose levels) to identify certain characteristic(s) of physiological data. Using the identified characteristics, the computer system may then calculate and track certain metrics that are critical in guiding treatment of a given chronic health condition in a personalized manner. In the case of diabetes, such metrics can include, for example, time-in-range (TIR), glycemic variability (GV), glycemic exposure, and/or ranges for hypoglycemia and hyperglycemia. The computer system can then use these tracked metrics to produce automatically a personalized health goal for the user. For example, based on the tracking, a glycemic range may be identified within which the user is expected to remain based on a TIR measure associated with a prior glycemic range. If it is determined that the user maintained a blood glucose level of 7.2-8.3 mmol/L (130-150 mg/dL) more than 83% percent of the time over the course of a week, the system may recommend that the user attempt to maintain a blood glucose level of 6.7-7.8 mmol/L (120-140 mg/dL) over the following week.

Example process 1200 continues at operation 1204 with determining contextual information associated with the user and/or detecting a change in the contextual information associated with the user (e.g., as described with respect to operations 1005 and/or 1009 of example process 1000) and at operation 1206 with determining that the contextual information and/or detected change is indicative of satisfaction of a milestone associated with the health goal. For example, operation 1204 may include detecting, based on received input data, that the user has performed an activity (e.g., walking a certain number of steps) and operation 1206 may include determining that the detected activity satisfies a milestone associated with the health goal. As another example, operation 1204 may include detecting, based on received input data, health state or change in health state of the user (e.g., a blood glucose level) and determining if the detected health state or change in health state satisfies a milestone associated with the health goal.

Example process 1200 continues at operation 1208 with dynamically updating presentation of the virtual sidekick to depict the virtual sidekick reacting to the user's satisfaction of the milestone associated with the health goal. In some embodiments, the reaction by the virtual sidekick may be configured to encourage the user to complete the health goal. For example, the reaction by the virtual sidekick may include a visual expression or gesture that emulate a supportive expression or gesture by a caretaker or another patient facing a substantially similar chronic condition as the user. In some embodiments, the reaction by the virtual sidekick may additionally include non-visual elements such as audible expression (verbal or non-verbal) output via speakers of the user's computing device. As an illustrative example, in response to detecting that the user has walked a certain number of steps in a day and determining that performance of this activity satisfies a milestone of a health goal, operation 1208 may include depicting a visual representation of the virtual sidekick smiling, giving a "thumbs up," expressing admiration of the user's accomplishment, putting on walking shoes and/or walking in solidarity, etc.

The virtual sidekick displayed via the GUI may be simulated using one or more computer programs executed by a computer system associated with a health management platform 102.

In some embodiments, a computer program operable to simulate the virtual sidekick may include instructions for performing one or more predefined interaction scripts in response to detected events or conditions. For example, the instructions associated with such as computer program may cause a visual representation of the virtual sidekick to depict the virtual sidekick performing a predefined action (e.g., walking) in response to detecting, based on input data, a condition or event (e.g., the user walking). The computer program may be configured with a plurality of predefined scripts used to dynamically update presentation of the virtual sidekick in the GUI in response to detected conditions or events such as a change in the contextual information associated with the user.

Alternatively, or in addition, the computer program used to simulate the virtual sidekick may include or utilize one or more artificial intelligence models. In such embodiments, input data (and/or contextual information) may be fed into an artificial intelligence model that generates outputs that cause the presentation of the virtual sidekick to dynamically update. Notably, in some embodiments, actions performed by the virtual sidekick based on processing using artificial intelligence models may not be according to predefined scripts. In some embodiments, such artificial intelligence models may apply machine learning techniques to learn how best to assist a user in managing a chronic condition. For example, a machine learning artificial intelligence model may be continually trained and updated based on updated input data received via a data pipeline 400. In some embodiments, a machine learning artificial intelligence model used to simulate the virtual sidekick may be specifically trained for use in assisting a particular user of the health management platform 102 by utilizing input data associated with that user as training data. In some embodiments, a machine learning artificial intelligence model used to simulate the virtual sidekick may be additionally trained based on input data associated with multiple other users (e.g., other patients) of the health management platform 102. For example, a machine learning artificial intelligence model may be specifically trained to assist a user in managing a specific chronic health condition such as diabetes by utilizing input data from multiple other users with the same or a substantially similar chronic health condition.

In some embodiments, a computer program used to simulate the virtual sidekick may be selected from a repository including multiple different computer programs based on input data received via a data pipeline 400. For example, when personalizing a virtual sidekick for a user, the health management platform 102 may process various input data associated with the user (e.g., patient survey data) and select, based on the input data, a computer program associated with a particular predefined virtual sidekick from a repository of multiple computer programs associated with multiple predefined virtual sidekicks. In this way, a configured program best suited to assist the user may be utilized to simulate the virtual sidekick. As an illustrative example, in response to determining that the user has diabetes, the health management platform 102 may select a particular computer program configured for simulating a virtual sidekick to assist a user that has diabetes. In such an example, the selected program may be pre-configured to simulate the virtual sidekick as having a substantially similar chronic health condition (e.g., diabetes) as the user.

In some embodiments, a computer program used to simulate the virtual sidekick may be configured based on input data and/or contextual information associated with the user. For example, the computer program may include one or more adjustable parameters that govern, for example, how certain predefined scripts are applied or how artificial intelligence models are applied. In such an embodiment, values for the one or more parameters may be adjusted to configure the computer program to personalize to the user. For example, the health platform 102 may identify, based on received input data, a chronic health condition of the user. In response to identifying the chronic health condition of the user, the health platform 102 may configure a computer program to simulate the virtual sidekick as having a substantially similar chronic health condition as the user.

In some embodiments, the computer program used to simulate the virtual sidekick is configured once during an initial stage before the virtual sidekick has begun assisting the user. For example, a user may input patient survey data when initially accessing the health management platform 102. The health management platform 102 may then use this input patient survey data to configure a computer program to simulate a virtual sidekick that is personalized to the user. In other embodiments, the computer program used to simulate the virtual sidekick may be configured and reconfigured continually over time as additional input data are received via the data pipeline. As an illustrative example, updated input data may be used to retrain one or more artificial intelligence models used to simulate the virtual sidekick. In other words, the computer program may be reconfigured as the user is accessing the health management platform 102 to best assist the user in managing his or her chronic health condition.

Processing System

Figure 13:
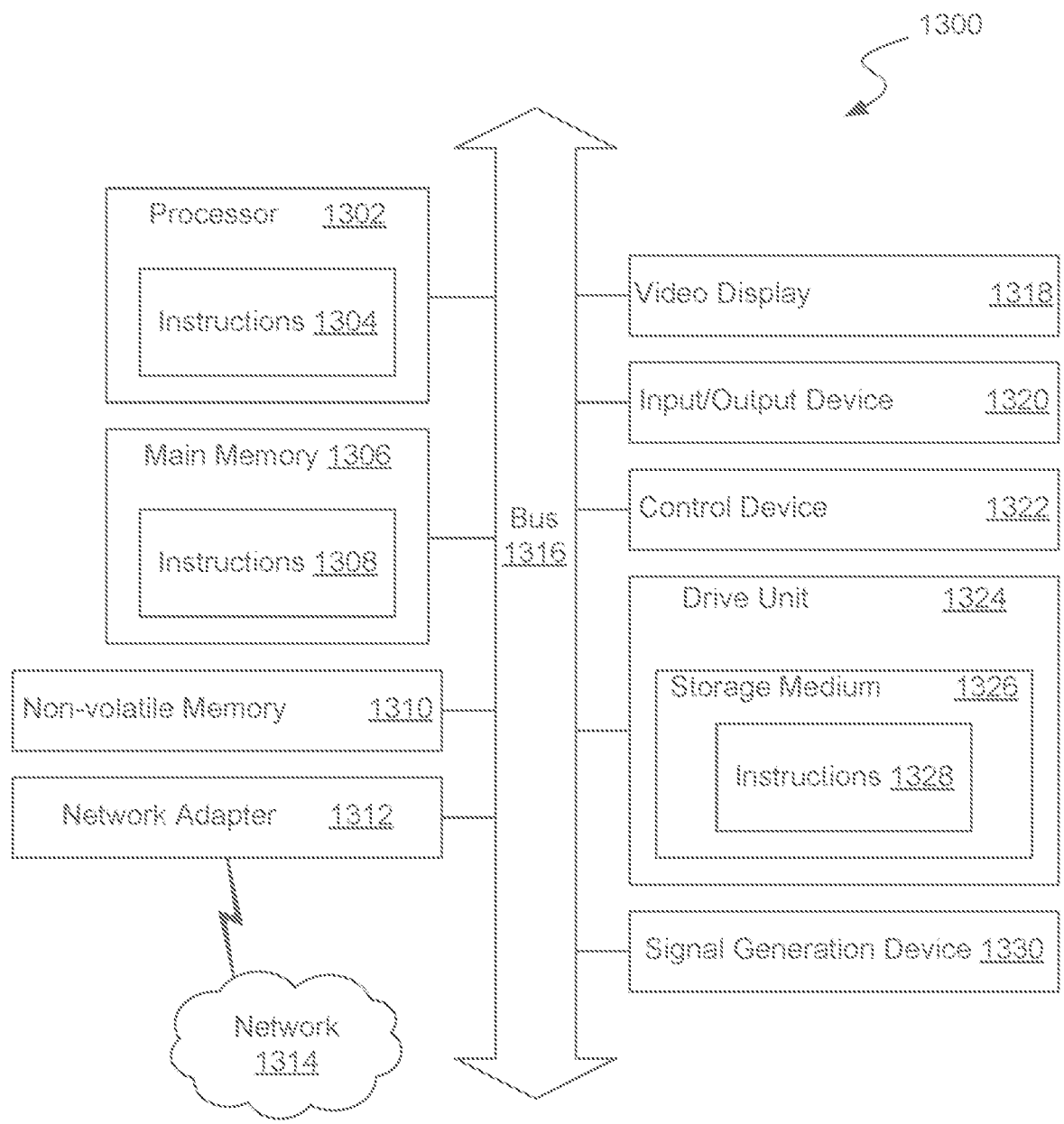
FIG. 13 shows a block diagram illustrating an example of a computer processing system in which at least some operations described herein can be implemented.

FIG. 13 is a block diagram illustrating an example of a processing system 1300 in which at least some operations described herein can be implemented. For example, some components of the processing system 1300 may be hosted on a computing device that includes a health management platform (e.g., health management platform 102 of FIG. 1).

The processing system 1300 may include one or more central processing units ("processors") 1302, main memory 1306, non-volatile memory 1310, network adapter 1312 (e.g., network interface), video display 1318, input/output devices 1320, control device 1322 (e.g., keyboard and pointing devices), drive unit 1324 including a storage medium 1326, and signal generation device 1330 that are communicatively connected to a bus 1316. The bus 1316 is illustrated as an abstraction that represents one or more physical buses and/or point-to-point connections that are connected by appropriate bridges, adapters, or controllers. The bus 1316, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The processing system 1300 may share a similar computer processor architecture as that of a desktop computer, tablet computer, personal digital assistant (PDA), mobile phone, game console (e.g., Sony PlayStation™ or Microsoft Xbox™), music player (e.g., Apple iPod Touch™), wearable electronic device (e.g., a watch or fitness tracker), network-connected ("smart") device (e.g., a television or home assistant device), virtual/augmented reality systems (e.g., a head-mounted display such as Oculus Rift™ or Microsoft Hololens™), or another electronic device capable of executing a set of instructions (sequential or otherwise) that specify action(s) to be taken by the processing system 1300.

While the main memory 1306, non-volatile memory 1310, and storage medium 1326 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 1328. The term "machine-readable medium" and "storage medium" shall also be taken to include any medium that is capable of storing, encoding, or carrying a set of instructions for execution by the processing system 1300.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 1304, 1308, 1328) set at various times in various memory and storage devices in a computing device. When read and executed by the one or more processors 1302, the instruction(s) cause the processing system 1300 to perform operations to execute elements involving the various aspects of the disclosure.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 1310, floppy and other removable disks, hard disk drives, optical disks (e.g., Compact Disc Read-Only Memory (CD-ROMS), Digital Versatile Discs (DVDs)), and transmission-type media such as digital and analog communication links.

The network adapter 1312 enables the processing system 1300 to mediate data in a network 1314 with an entity that is external to the processing system 1300 through any communication protocol supported by the processing system 1300 and the external entity. The network adapter 1312 can include a network adaptor card, a wireless network interface card, a router, an access point, a wireless router, a switch, a multilayer switch, a protocol converter, a gateway, a bridge, bridge router, a hub, a digital media receiver, and/or a repeater.

The network adapter 1312 may include a firewall that governs and/or manages permission to access/proxy data in a computer network, and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall may additionally manage and/or have access to an access control list that details permissions including the access and operation rights of an object by an individual, a machine, and/or an application, and the circumstances under which the permission rights stand.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

Remarks

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. A method comprising:
  causing, by a computer system, display of a graphical user interface (GUI) at a user computing device,
    wherein the computer system is associated with a health management platform;
  receiving, by the computer system, input data from a plurality of data sources; and
  presenting, by the computer system based on the input data, a virtual sidekick that is configured to recommend an action in an effort to assist a user in managing a chronic health condition in the GUI,
    wherein the virtual sidekick is presented in a virtual scene including a reverse augmented reality element indicative of a physical context associated with the user, and
    wherein the reverse augmented reality element is a graphical element that is indicative of a physical location of the user, a weather condition at the physical location, an object in proximity to the user, or an activity performed by the user.

2. The method of claim 1, further comprising:
  receiving, by the computer system, updated input data from one or more of the plurality of data sources; and
  dynamically updating, by the computer system, presentation of the virtual sidekick in response to and based on the updated input data.

3. The method of claim 2, further comprising:
  determining, by the computer system based on the input data, contextual information associated with the user, wherein the contextual information includes information indicative of any one or more of: the chronic health condition of the user, a health state of the user, a mood of the user, an activity performed by the user, the physical location of the user, or the weather condition at the physical location;
  wherein presentation of the virtual sidekick is based on the contextual information associated with the user; and
  detecting, by the computer system, a change in the contextual information associated with the user as the updated input data are received from the one or more of the plurality of data sources;

wherein presentation of the virtual sidekick is dynamically updated in response to detecting the change in the contextual information associated with the user.

4. The method of claim 1, wherein presenting the virtual sidekick includes:
simulating the virtual sidekick using a computer program, the computer program including any one or more of:
a predefined user interaction script; or
an artificial intelligence model.

5. The method of claim 1, wherein presenting the virtual sidekick includes:
selecting, based on the input data, a computer program associated with a particular predefined virtual sidekick from a plurality of computer programs associated with a plurality of predefined virtual sidekicks; and
simulating the virtual sidekick using the selected computer program.

6. The method of claim 1, further comprising:
identifying, by the computer system based on the input data, the chronic health condition of the user,
wherein presenting the virtual sidekick includes:
configuring a computer program to simulate the virtual sidekick as having a substantially similar chronic health condition as the user; and
simulating the virtual sidekick using the configured computer program.

7. The method of claim 1, further comprising:
determining, by the computer system based on physiological data included in the input data, a health state of the user;
wherein presentation of the virtual sidekick includes a visual representation of the virtual sidekick based on the health state of the user.

8. The method of claim 7, wherein the visual representation of the virtual sidekick corresponds to the health state of the user.

9. The method of claim 7, further comprising:
identifying, by the computer system, a predefined activity to improve the health state of the user; and
dynamically updating, by the computer system, the visual representation of the virtual sidekick to depict the virtual sidekick performing or attempting to perform the predefined activity.

10. The method of claim 9, wherein dynamically updating the visual representation of the virtual sidekick to depict the virtual sidekick performing or attempting to perform the predefined activity includes dynamically adjusting the visual representation of the virtual sidekick to depict the virtual sidekick making a mistake while performing or attempting to perform the predefined activity.

11. The method of claim 10, wherein the predefined activity includes any of:
using a health monitoring device to acquire updated physiological data;
performing a fitness activity; or
swapping a first food item for a second food item in a meal.

12. The method of claim 1, further comprising:
determining, by the computer system based on the input data, a health goal for the user,
wherein the health goal is associated with management of the chronic health condition of the user;
receiving, by the computer system, updated input data from one or more of the plurality of data sources;
detecting, by the computer system based on the updated input data, an activity performed by the user; and determining, by the computer system, that the activity performed by the user satisfies a milestone associated with the health goal; and
dynamically updating, by the computer system, a visual representation of the virtual sidekick to depict a reaction by the virtual sidekick to the activity performed by the user,
wherein the reaction by the virtual sidekick is configured to encourage the user to complete the health goal.

13. The method of claim 12, wherein the reaction by the virtual sidekick includes a visual expression by the virtual sidekick that emulates a supportive expression by a caretaker or another person with a substantially similar chronic health condition as the user.

14. The method of claim 1, further comprising:
receiving, by the computer system, updated input data from one or more of the plurality of data sources;
detecting, by the computer system based on the updated input data, a first activity performed by the user; and
dynamically updating, by the computer system, a visual representation of the virtual sidekick to depict the virtual sidekick performing a second activity that corresponds to the first activity performed by the user.

15. The method of claim 14, wherein the second activity:
mirrors the first activity; or
is a response to the first activity.

16. The method of claim 1, further comprising:
determining, by the computer system based on location data included in the input data, the physical location of the user,
wherein the location data are received from the user computing device;
wherein the reverse augmented reality element is indicative of the physical location of the user.

17. The method of claim 1, further comprising:
determining, by the computer system based on weather data included in the input data, the weather condition at the physical location of the user;
wherein the reverse augmented reality element is indicative of the weather condition at the physical location of the user.

18. The method of claim 1, further comprising:
determining, by the computer system based on physiological data included in the input data, a health state of the user; and
identifying, by the computer system, a predefined activity to improve the health state of the user,
wherein the predefined activity is associated with the object in proximity to the user;
wherein the reverse augmented reality element is indicative of the object associated with the predefined activity.

19. The method of claim 18, wherein the predefined activity is an exercise activity and wherein the object associated with the exercise activity is an exercise equipment.

20. The method of claim 18, wherein the predefined activity is a food swap activity and wherein the object is a food item.

21. The method of claim 18, wherein the predefined activity is a health measurement activity and wherein the object is a health monitoring device used to perform the health measurement activity.

22. The method of claim 1, wherein the input data includes any one or more of:

an input received from the user computing device, the input based on an interaction by the user with the GUI at the user computing device;
physiological data received from a health monitoring device;
fitness data received from a fitness tracking device;
sensor data received from a sensor device;
location data received from the user computing device; or
weather data received from an online weather service.

23. The method of claim 1, wherein the virtual sidekick is presented as an animated character.

24. A computer system comprising:
a processor; and
a memory coupled to the processor, the memory including instructions, which when executed by the processor, cause the computer system to:
cause display of a graphical user interface (GUI) at a user computing device,
wherein the computer system is associated with a health management platform;
receive input data from a plurality of data sources, the input data including contextual information associated with a user of the user computing device; and
present, based on the input data, a virtual sidekick that is configured to recommend an action in an effort to assist the user in managing a chronic health condition in the GUI,
wherein the virtual sidekick is presented in a virtual scene including a reverse augmented reality element indicative of a physical context associated with the user, and
wherein the reverse augmented reality element is a digitally presented element that is indicative of a physical location of the user, a weather condition at the physical location, an object in proximity to the user, or an activity performed by the user.

25. A non-transitory computer-readable medium with instructions stored thereon that, when executed by a processor, cause the processor to perform operations comprising:
causing display of a graphical user interface (GUI) at a user computing device,
wherein the computer system is associated with a health management platform;
receiving input data from a plurality of data sources, the input data including contextual information associated with a user of the user computing device; and
presenting, based on the input data, a virtual sidekick that is configured to recommend an action in an effort to assist the user in managing a chronic health condition,
wherein the virtual sidekick is presented in a virtual scene including a reverse augmented reality element indicative of a physical context associated with the user, and
wherein the reverse augmented reality element is a multimedia element that is indicative of a physical location of the user, a weather condition at the physical location, an object in proximity to the user, or an activity performed by the user.

* * * * *